(12) United States Patent
Selic et al.

(10) Patent No.: US 10,323,056 B2
(45) Date of Patent: Jun. 18, 2019

(54) CRYSTALLINE HYDRATES OF 1-(β-D-GLUCOPYRANOSYL)-4-METHYL-3-[5-(4-FLUOROPHENYL)-2-THIENYLMETHYL]BENZENE

(71) Applicant: Lek Pharmaceuticals d.d., Ljubljana (SI)

(72) Inventors: Lovro Selic, Ljubljana (SI); Andreas Hotter, Kundl/Tirol (AT); Christoph Langes, Innsbruck (AT); Ulrich Griesser, Innsbruck (AT)

(73) Assignee: Lek Pharmaceuticals d.d., Ljubljana (SI)

( * ) Notice: Subject to any disclaimer, the term of this patent is extended or adjusted under 35 U.S.C. 154(b) by 0 days.

(21) Appl. No.: 14/888,961

(22) PCT Filed: May 7, 2014

(86) PCT No.: PCT/EP2014/059281
§ 371 (c)(1),
(2) Date: Nov. 4, 2015

(87) PCT Pub. No.: WO2014/180872
PCT Pub. Date: Nov. 13, 2014

(65) Prior Publication Data
US 2016/0145286 A1     May 26, 2016

(30) Foreign Application Priority Data

May 8, 2013  (EP) .................................. 13166940
Feb. 14, 2014 (EP) .................................. 14155190

(51) Int. Cl.
| C07D 409/10 | (2006.01) |
| C07H 7/04 | (2006.01) |
| A61K 31/155 | (2006.01) |
| A61K 31/7034 | (2006.01) |

(52) U.S. Cl.
CPC ............ *C07H 7/04* (2013.01); *A61K 31/155* (2013.01); *A61K 31/7034* (2013.01); *C07D 409/10* (2013.01); *C07B 2200/13* (2013.01)

(58) Field of Classification Search
None
See application file for complete search history.

(56) References Cited

U.S. PATENT DOCUMENTS

| 8,535,715 | B2 * | 9/2013 | Abebe | ................ | A61K 9/209 |
| | | | | | 424/465 |
| 8,999,941 | B2 * | 4/2015 | Henschke | ............ | C07D 409/00 |
| | | | | | 514/23 |

FOREIGN PATENT DOCUMENTS

| WO | 2005012326 A1 | 2/2005 |
| WO | 2008069327 A1 | 6/2008 |
| WO | 2009035969 A1 | 3/2009 |
| WO | 2010043682 A2 | 4/2010 |
| WO | 2011003976 A1 | 1/2011 |
| WO | 2011047113 A1 | 4/2011 |
| WO | 2012154812 A1 | 11/2012 |
| WO | 2013064909 S2 | 5/2013 |

OTHER PUBLICATIONS

Authelin et al., "Thermodynamics of non-stoichiometric pharmaceutical hydrates" International Journal of Pharmaceutics (2005) vol. 303 pp. 37-53.*
Lieberman et al., Pharmaceutical Dosage Forms, Second Edition, vol. 2, published 1990 by Marcel Dekker, Inc, pp. 462-472.*
Braga et al., "Making Crystals from Crystals: a green route to crystal engineering and polymorphism" Chemical Communications (2005) pp. 3635-3645.*
Vippagunta et al., "Crystalline Solids" Advanced Drug Delivery Reviews (2001) vol. 48 pp. 3-26.*
Jain et al., "Polymorphism in Pharmacy" Indian Drugs (1986) vol. 23 No. 6 pp. 315-329.*
Witschi et al., "Residual solvents in pharmaceutical products: acceptable limits, influences on physicochemical properties, analytical methods, and documented values." European Journal of Pharmaceutica and Biopharmaceutics (1997) vol. 43 pp. 215-242 (Year: 1997).*
Dwivedi, Anil, "Residual Solvent Analysis in Pharmaceuticals" Pharmaceutical Technology (Nov. 2002) pp. 42-46 (Year: 2002).*
Braga et al., "Making Crystals from Crystals: a green route to crystal engineering and polymorphism" Chem Commun (2005) pp. 3635-3645 (Year: 2005).*
Jain et al., "Polymorphism in Pharmacy" Indian Drugs (1986) vol. 23 No. 6 pp. 315-328 (Year: 1986).*
Lieberman et al., "Pharmaceutical Dosage Forms vol. 2" published 1990 by Marcel Dekker, Inc pp. 467-472 (Year: 1990).*
Gu, Chong-Hui, et al., Polymorph Screening: Influence of Solvents on the Rate of Solvent-Mediated Polymorphic Transformation, Journal of Pharmaceutical Sciences, Nov. 2001, pp. 1878-1890, vol. 90, Issue 11.

* cited by examiner

*Primary Examiner* — Eric Olson
(74) *Attorney, Agent, or Firm* — Luedeka Neely Group, P.C.

(57) ABSTRACT

The present invention relates to non-stoichiometric crystalline hydrates of 1-(β-D-glucopyranosyl)-4-methyl-3-[5-(4-fluorophenyl)-2-thienylmethyl]benzene, processes for their preparation, and their use as medicaments. In addition the present invention relates to pharmaceutical compositions comprising an effective amount of the novel crystalline hydrates.

15 Claims, 7 Drawing Sheets

CRYSTALLINE HYDRATES OF 1-(β-D-GLUCOPYRANOSYL)-4-METHYL-3-[5-(4-FLUOROPHENYL)-2-THIENYL-METHYL]BENZENE

This application is a national phase entry of PCT International application number PCT/EP2014/059281, filed May 7, 2014. This application also claims the benefit of the earlier filing date of EP 13166940.0, filed May 8, 2013 and of EP 14155190.3, filed Feb. 14, 2014.

FIELD OF THE INVENTION

The present invention relates to novel crystalline hydrates of 1-(β-D-glucopyranosyl)-4-methyl-3-[5-(4-fluorophenyl)-2-thienylmethyl]benzene, processes for their preparation, and their use as medicaments. In addition the present invention relates to pharmaceutical compositions comprising an effective amount of the novel crystalline hydrates.

BACKGROUND OF THE INVENTION 1-(β-D-glucopyranosyl)-4-methyl-3-[5-(4-fluorophenyl)-2-thienylmethyl]benzene, also known as canagliflozin, belongs to a novel therapeutic class of sodium-glucose co-transporter 2 inhibitors. US drug regulatory approval was received in March 2013 (INVOKANA™) for canagliflozin as an adjunct to diet and exercise to improve glycemic control in adults with type-2 diabetes mellitus. 1-(β-D-glucopyranosyl)-4-methyl-3-[5-(4-fluorophenyl)-2-thienylmethyl]benzene is represented by the following general formula (I):

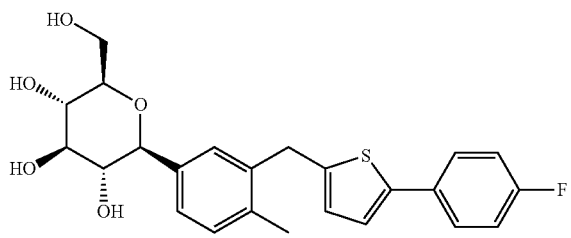

(I)

WO 2005/012326 A1 discloses the compound of formula (I) per se. A procedure for the preparation of the compound of formula (I) is disclosed generically in example 1 of the same application. However, the application is silent about the solid state form obtained.

WO 2008/069327 A1 discloses a crystalline hemihydrate of the compound of formula (I) and a process for the preparation thereof.

WO 2009/035969 A1 discloses a crystalline form of the compound of formula (I). An overlay of the X-ray powder diffractograms of the crystalline form of the compound of formula (I) provided in FIG. 1 of WO 2009/035969 A1 and the crystalline form of the compound of formula (I) provided in FIG. 1 of WO 2008/069327 A1 shows good agreement, confirming the presence of the same solid state form, namely the crystalline hemihydrate. In addition a process for preparing the crystalline hemihydrate of the compound of formula (I) is disclosed. WO 2010/043682 A2 discloses a process for preparing the crystalline hemihydrate of the compound of formula (I).

WO 2011/003976 A1 discloses a process for preparing the crystalline hemihydrate of the compound of formula (I) having a narrow particle size distribution, wherein a suspension of the hemihydrate of formula (I) in an organic solvent or a mixture of an organic solvent and water is subjected to at least one temperature oscillation and at least one mechanical particle size reduction step.

WO 2012/154812 A1 discloses co-crystals of the compound of formula (I) with L-proline and citric acid and methods for their preparation.

WO 2013/064909 A2 discloses amorphous 1-(β-D-glucopyranosyl)-4-methyl-3-[5-(4-fluorophenyl)-2-thienylmethyl]benzene as well as co-crystals of the compound of formula (I) with L-proline, D-proline and L-phenylalanine. Processes for the preparation of these solid forms are also disclosed in the application.

According to the prior art literature, 1-(β-D-glucopyranosyl)-4-methyl-3-[5-(4-fluorophenyl)-2-thienylmethyl]benzene hemihydrate is obtained by crystallization/precipitation from an organic solvent containing some water and optionally an organic antisolvent. However, the use of organic solvents and organic antisolvents in crystallization processes is associated with certain drawbacks as they are often expensive, toxic and/or harmful to health and/or the environment. In addition, residual organic solvents are often not completely removed from active pharmaceutical ingredients by practical manufacturing techniques. Nevertheless, they should be decreased to a minimum amount as these residual solvents show no therapeutic effect and are mostly toxic. Therefore, an environmentally friendly crystallization process for the preparation of crystalline 1-(β-D-glucopyranosyl)-4-methyl-3-[5-(4-fluorophenyl)-2-thienylmethyl]benzene free of organic solvents and consequently a product obtained from this process lacking residual organic solvents is highly desirable.

Furthermore, WO 2008/069327 A1 mentions that amorphous 1-(β-D-glucopyranosyl)-4-methyl-3-[5-(4-fluorophenyl)-2-thienylmethyl]benzene suffers from stability and handling issues such as poor filterability. Therefore, crystalline 1-(β-D-glucopyranosyl)-4-methyl-3-[5-(4-fluorophenyl)-2-thienylmethyl]benzene is preferred since it is, for example, more stable and easier to isolate. In addition, the bioavailability of a compound intended to be administered orally is dependent on the compound's solubility and permeability according to the Biopharmaceutical Classification System. Thus a crystalline form of 1-(β-D-glucopyranosyl)-4-methyl-3-[5-(4-fluorophenyl)-2-thienylmethyl]benzene having increased solubility and consequently increased oral bioavailability is desirable.

SUMMARY OF THE INVENTION

The inventors of the present invention have found novel crystalline hydrates of 1-(β-D-glucopyranosyl)-4-methyl-3-[5-(4-fluorophenyl)-2-thienylmethyl]benzene which can be prepared from water alone without the need of organic solvents. This is surprising because, according to the prior art literature, the use of an organic solvent would appear to be a prerequisite for the production of crystalline 1-(β-D-glucopyranosyl)-4-methyl-3-[5-(4-fluorophenyl)-2-thienylmethyl]benzene. Indeed, given that 1-(β-D-glucopyranosyl)-4-methyl-3-[5-(4-fluorophenyl)-2-thienylmethyl]benzene is practically insoluble in water, it is surprising that crystalline hydrates can be obtained from amorphous material suspended in water (Gu et al., Journal of Pharmaceutical Sciences, Vol. 90, No. 11, November 2001, pages 1878-1890). The hydrates of the present invention are free of any residual organic solvents due to the organic solvent-free production processes. This is regarded as a significant advantage compared to previously produced forms of this active pharmaceutical ingredient (API). In addition, the production processes for the novel hydrates are cheap, safe and environmentally friendly.

The novel hydrates of the present invention also show favorable physicochemical properties. For example, they are chemically stable, have favorable crystal habits and therefore show good handling properties such as good isolation, drying, flow and compaction properties. In addition, the novel hydrates show better aqueous solubilities than the known 1-(β-D-glucopyranosyl)-4-methyl-3-[5-(4-fluorophenyl)-2-thienylmethyl]benzene hemihydrate disclosed in WO 2008/069327 A1 and, therefore, possess higher bioavailabilities when administered orally according to the Biopharmaceutical Classification System.

The novel hydrates of the present invention are non-stoichiometric hydrates, which means that the actual water content of the sample depends on the humidity of the surrounding atmosphere.

Hence, in a first aspect, the present invention relates to a crystalline form of a non-stoichiometric hydrate of 1-(β-D-glucopyranosyl)-4-methyl-3-[5-(4-fluorophenyl)-2-thienylmethyl]benzene.

In one embodiment, the present invention relates to a crystalline form of a non-stoichiometric hydrate of 1-(β-D-glucopyranosyl)-4-methyl-3-[5-(4-fluorophenyl)-2-thienylmethyl]benzene, referred to herein as form HxA, characterized by an X-ray powder diffractogram comprising characteristic peaks at 2-theta angles of 5.4±0.2°, 6.7±0.2°, 13.2±0.2°, 16.1±0.2°, 19.6±0.2° and 24.1±0.2°.

In another embodiment, the present invention relates to a crystalline form of a non-stoichiometric hydrate of 1-(β-D-glucopyranosyl)-4-methyl-3-[5-(4-fluorophenyl)-2-thienylmethyl]benzene, referred to herein as form HxB, characterized by an X-ray powder diffractogram comprising characteristic peaks at 2-theta angles of 6.6±0.2°, 7.3±0.2°, 12.2±0.2°, 15.4±0.2°, 19.9±0.2° and 23.9±0.2°.

In a second aspect, the present invention relates to a process for the preparation of a crystalline form of a non-stoichiometric hydrate of 1-(β-D-glucopyranosyl)-4-methyl-3-[5-(4-fluorophenyl)-2-thienylmethyl]benzene comprising the steps of:
  (a) forming a suspension of amorphous 1-(β-D-glucopyranosyl)-4-methyl-3-[5-(4-fluorophenyl)-2-thienylmethyl]benzene in water;
  (b) subjecting the obtained suspension to a particle size reduction process; and
  (c) isolating the obtained crystals.

The crystalline non-stoichiometric hydrate HxA of 1-(β-D-glucopyranosyl)-4-methyl-3-[5-(4-fluorophenyl)-2-thienylmethyl]benzene is prepared by subjecting the crystals obtained in step (c) to an atmosphere having a relative humidity of ≤30%.

The crystalline non-stoichiometric hydrate HxB of 1-(β-D-glucopyranosyl)-4-methyl-3-[5-(4-fluorophenyl)-2-thienylmethyl]benzene is prepared by subjecting the crystals obtained in step (c) to an atmosphere having a relative humidity of ≥45%.

In a third aspect, the present invention relates to an economical and industrially applicable process for the preparation of a crystalline form of a non-stoichiometric hydrate of the compound of formula (I) (1-(β-D-glucopyranosyl)-4-methyl-3-[5-(4-fluorophenyl)-2-thienyl-methyl]benzene) comprising the steps of:
  (i) forming a suspension (U) comprising water and seed crystals of the compound of formula (I),
  (ii) forming a solution (O) comprising a water-miscible organic solvent and the compound of formula (I),
  (iii) forming a mixture (M) comprising not more than 13 volume % of a water-miscible organic solvent by combining solution (O) and suspension (U) and
  (iv) crystallizing the compound of formula (I).

The seed crystals used in step (i) of the process can be obtained, for example, by following the process of the second aspect described above.

The crystalline non-stoichiometric hydrate HxA of 1-(β-D-glucopyranosyl)-4-methyl-3-[5-(4-fluorophenyl)-2-thienylmethyl]benzene is prepared by isolating the crystals obtained in step (iv) and subjecting them to an atmosphere having a relative humidity of ≤30%.

The crystalline non-stoichiometric hydrate HxB of 1-(β-D-glucopyranosyl)-4-methyl-3-[5-(4-fluorophenyl)-2-thienylmethyl]benzene is prepared by isolating the crystals obtained in step (iv) and subjecting them to an atmosphere having a relative humidity of ≥45%.

In a fourth aspect, the present invention relates to a pharmaceutical composition comprising an effective amount of a crystalline form of a non-stoichiometric hydrate of 1-(β-D-glucopyranosyl)-4-methyl-3-[5-(4-fluorophenyl)-2-thienylmethyl]benzene and a pharmaceutically acceptable carrier.

In a fifth aspect, the present invention relates to a crystalline form of a non-stoichiometric hydrate of 1-(β-D-glucopyranosyl)-4-methyl-3-[5-(4-fluorophenyl)-2-thienylmethyl]benzene for use as a medicament, for example in the treatment of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis and/or hypertension In a sixth aspect, the present invention relates to a pharmaceutical combination comprising a crystalline form of a non-stoichiometric hydrate of 1-(β-D-glucopyranosyl)-4-methyl-3-[5-(4-fluorophenyl)-2-thienylmethyl]benzene and metformin.

In the context of the present invention the following abbreviations have the indicated meaning, unless explicitly stated otherwise:
API active pharmaceutical ingredient
BCS biopharmaceutical classification system
DSC differential scanning calorimetry
ERH equilibrium relative humidity
HDPE high-density polyethylene
RH relative humidity
RT room temperature
TGA thermogravimetric analysis
XRPD x-ray powder diffraction/diffractogram

DETAILED DESCRIPTION OF THE INVENTION

As used herein the term "room temperature" indicates that the applied temperature is not critical and that no exact temperature value has to be kept. Usually, "room temperature" is understood to mean temperatures between 15 and 25° C. [see e.g. European Pharmacopoeia 7.7, 1.2 (2013)].

The term "non-stoichiometric hydrate" as used herein refers to a crystalline form containing crystal water in a non-stoichiometric manner, whereat the amount of water incorporated into the crystal lattice depends on the environmental relative humidity.

The term "stoichiometric hydrate" as used herein refers to a crystalline form containing crystal water in a stoichiometric manner, whereat the amount of water incorporated into the crystal lattice is essentially independent on the environmental relative humidity. Small variations in the water content are e.g. due to adsorption or desorption of surface water.

Figure 5:
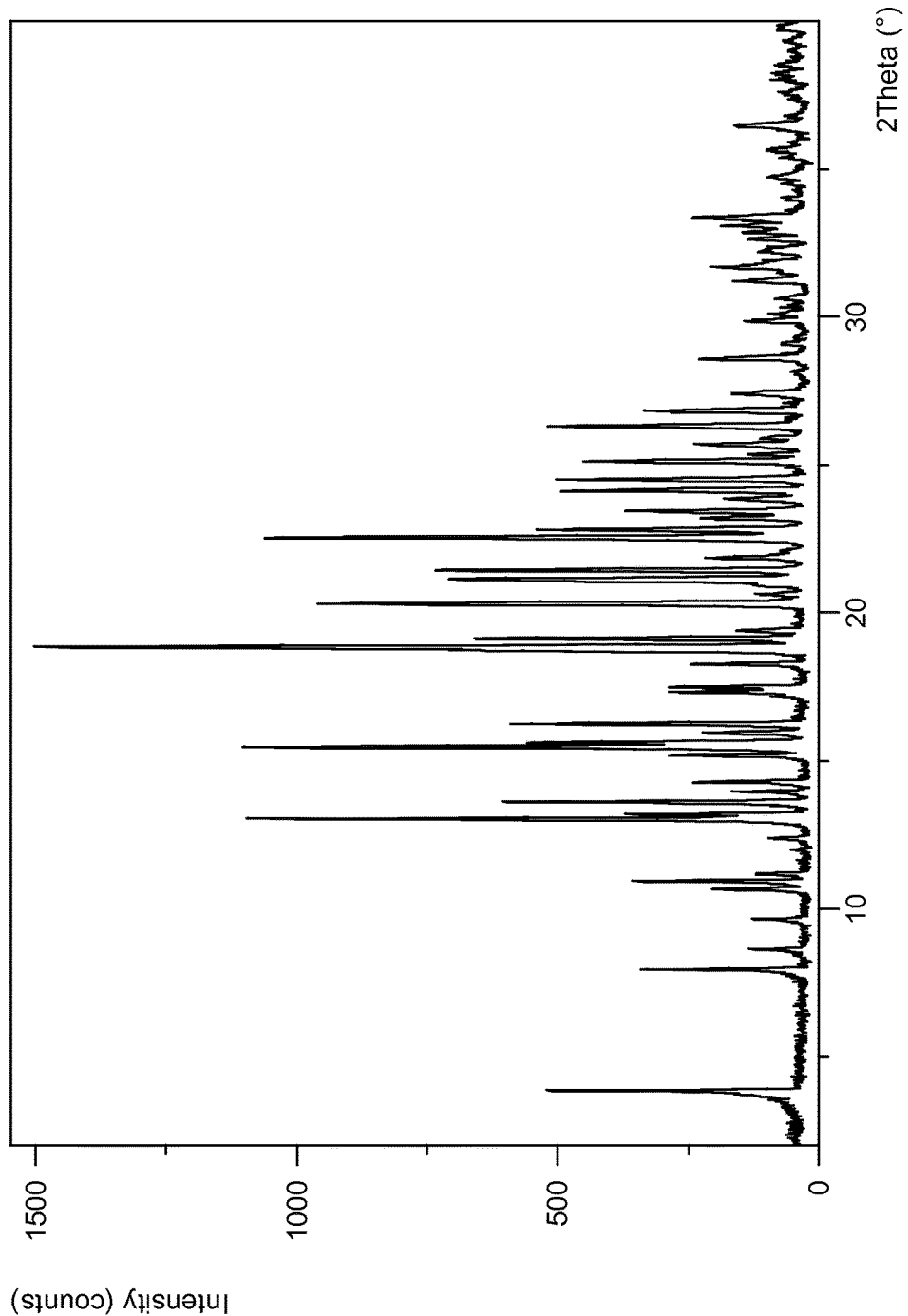
FIG. 5: XRPD of 1-(β-D-glucopyranosyl)-4-methyl-3-[5-(4-fluorophenyl)-2-thienylmethyl]benzene form Hy0.5 prepared according to Reference Example 2

The term "form Hy0.5" as used herein refers to the crystalline 1-(β-D-glucopyranosyl)-4-methyl-3-[5-(4-fluorophenyl)-2-thienylmethyl]benzene hemihydrate disclosed in WO 2008/069327 A1. Form Hy0.5 comprises characteristic XRPD peaks at 2-Theta angles of 3.9±0.2°, 13.0±0.2°, 15.5±0.2°, 18.8±0.2° and 20.3±0.2° and shows substantially the same XRPD as displayed in FIG. 5 when measured at room temperature using Cu-Kα radiation having a wavelength of 0.15419 nm.

The term "substantially the same" with reference to XRPD means that variabilities in peak positions and relative intensities of the peaks are to be taken into account. For example, a typical precision of the 2-Theta values is in the range of ±0.2° 2-Theta. Thus, the diffraction peak of form Hy0.5 that usually appears at 3.9° 2-Theta for example can appear between 3.7° and 4.1° 2-Theta on most X-ray diffractometers under standard conditions. Furthermore, one skilled in the art will appreciate that relative peak intensities will show inter-apparatus variability as well as variability due to degree of crystallinity, preferred orientation, sample preparation and other factors known to those skilled in the art and should be taken as qualitative measure only.

The inventors of the present invention have found novel crystalline hydrates of 1-(β-D-glucopyranosyl)-4-methyl-3-[5-(4-fluorophenyl)-2-thienylmethyl]benzene. The novel crystalline hydrates of 1-(β-D-glucopyranosyl)-4-methyl-3-[5-(4-fluorophenyl)-2-thienylmethyl]benzene of the present invention are non-stoichiometric hydrates comprising a water content in the range of about 0.1% (at a RH of about 0%) to about 8.0% (at a RH of about 95%) as determined by gravimetric moisture sorption/desorption and TGA.

Hence in a first aspect, the present invention relates to crystalline forms of a non-stoichiometric hydrate of 1-(β-D-glucopyranosyl)-4-methyl-3-[5-(4-fluorophenyl)-2-thienylmethyl]benzene.

In one embodiment, the present invention relates to crystalline forms of a non-stoichiometric hydrate of 1-(β-D-glucopyranosyl)-4-methyl-3-[5-(4-fluorophenyl)-2-thienylmethyl]benzene comprising a water content in the range of about 0.1 to 8.0%.

In another embodiment, the present invention relates to a novel crystalline form of a non-stoichiometric hydrate of 1-(β-D-glucopyranosyl)-4-methyl-3-[5-(4-fluorophenyl)-2-thienylmethyl]benzene (hereinafter also referred to as form HxA), characterized by an X-ray powder diffractogram comprising characteristic peaks at 2-theta angles of 5.4±0.2°, 6.7±0.2°, 13.2±0.2°, 16.1±0.2°, 19.6±0.2° and 24.1±0.2°.

Figure 1:
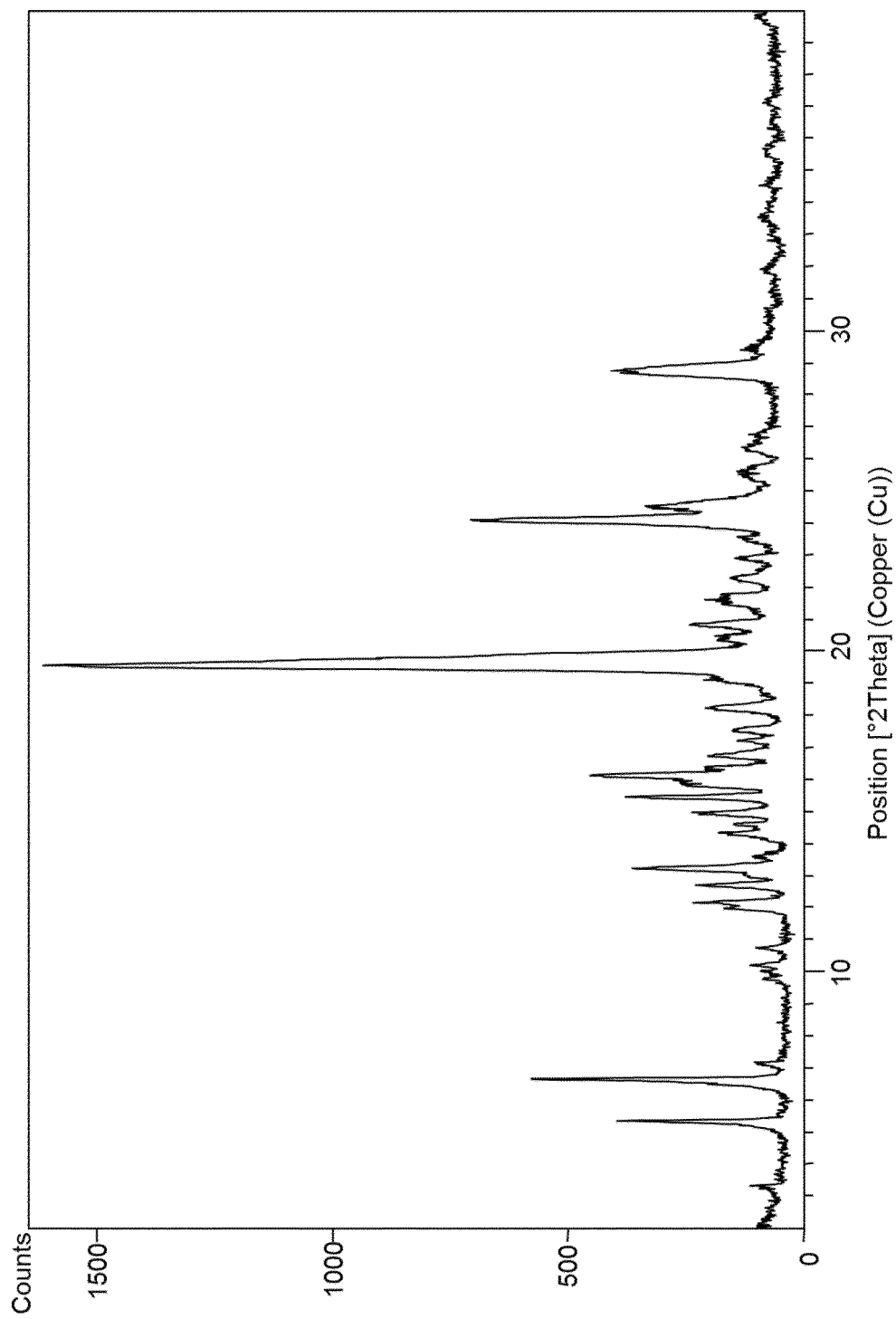
FIG. 1: XRPD of 1-(β-D-glucopyranosyl)-4-methyl-3-[5-(4-fluorophenyl)-2-thienylmethyl]benzene hydrate form HxA

The X-ray powder diffractogram of form HxA comprises additional characteristic peaks at 2-theta angles of 12.2±0.2°, 12.7±0.2°, 15.0±0.2°, 15.5±0.2°, 16.4±0.2°, 16.7±0.2°, 18.2±0.2°, 20.8±0.2°, 24.5±0.2° and 28.8±0.2°. A representative diffractogram is shown in FIG. 1. Therefore, in one embodiment, the present invention relates to a crystalline form of a non-stoichiometric hydrate of 1-(β-D-glucopyranosyl)-4-methyl-3-[5-(4-fluorophenyl)-2-thienylmethyl]benzene which has an X-ray powder diffraction pattern substantially the same as the X-ray powder diffraction pattern shown in FIG. 1 when measured using CuKα radiation.

Figure 2:
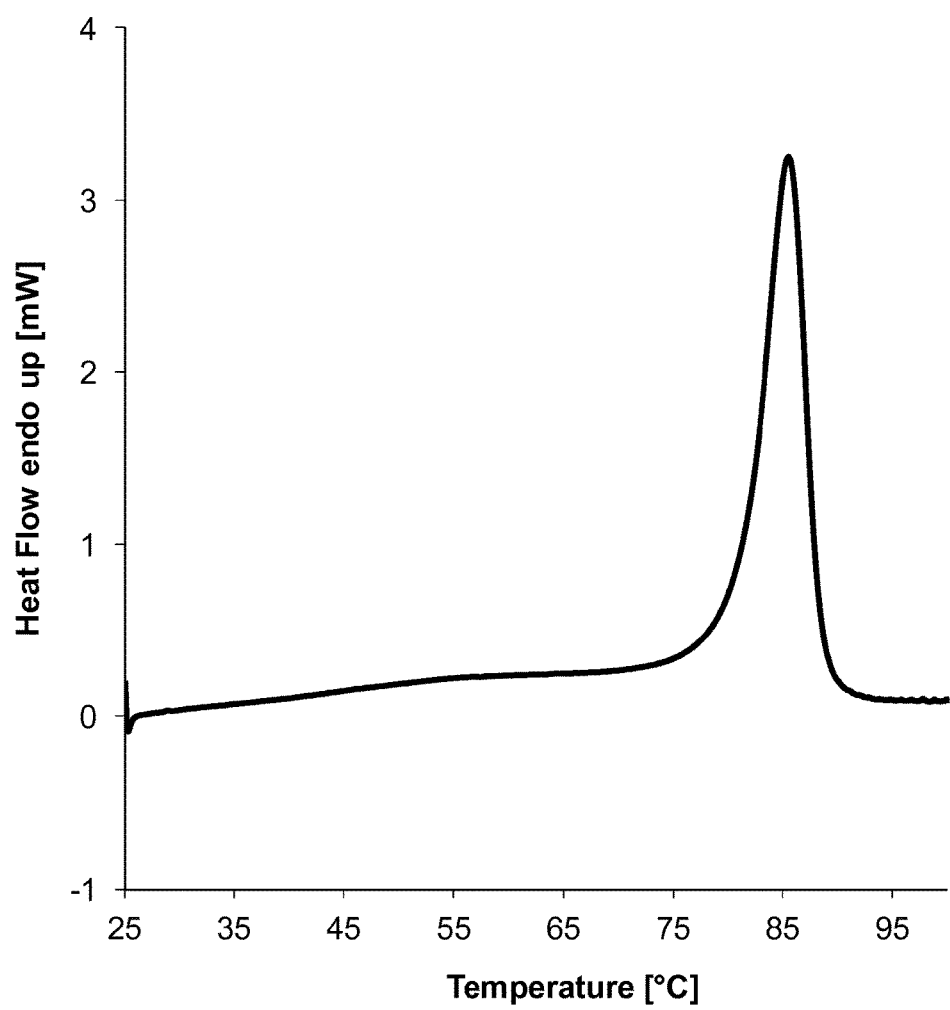
FIG. 2: DSC curve of 1-(β-D-glucopyranosyl)-4-methyl-3-[5-(4-fluorophenyl)-2-thienylmethyl]benzene hydrate form HxA

Moreover, form HxA can be characterized by a melting point having a peak maximum at about 86-87° C. determined by DSC at a heating rate of 5° C./min. A representative DSC thermogram is shown in FIG. 2.

Form HxA is a crystalline non-stoichiometric hydrate comprising a water content in the range of about 0.1 to 3.5%. For example, form HxA has a water content of about 0.1% at a RH of about 0% and a water content of about 3.5% at a RH of about 30% as determined by gravimetric moisture sorption/desorption and TGA.

In another embodiment, the present invention relates to a novel crystalline form of a non-stoichiometric hydrate of 1-(β-D-glucopyranosyl)-4-methyl-3-[5-(4-fluorophenyl)-2-thienylmethyl]benzene (hereinafter also referred to as form HxB), characterized by an X-ray powder diffractogram comprising characteristic peaks at 2-theta angles of 6.6±0.2°, 7.3±0.2°, 12.2±0.2°, 15.4±0.2°, 19.9±0.2° and 23.9±0.2°.

Figure 3:
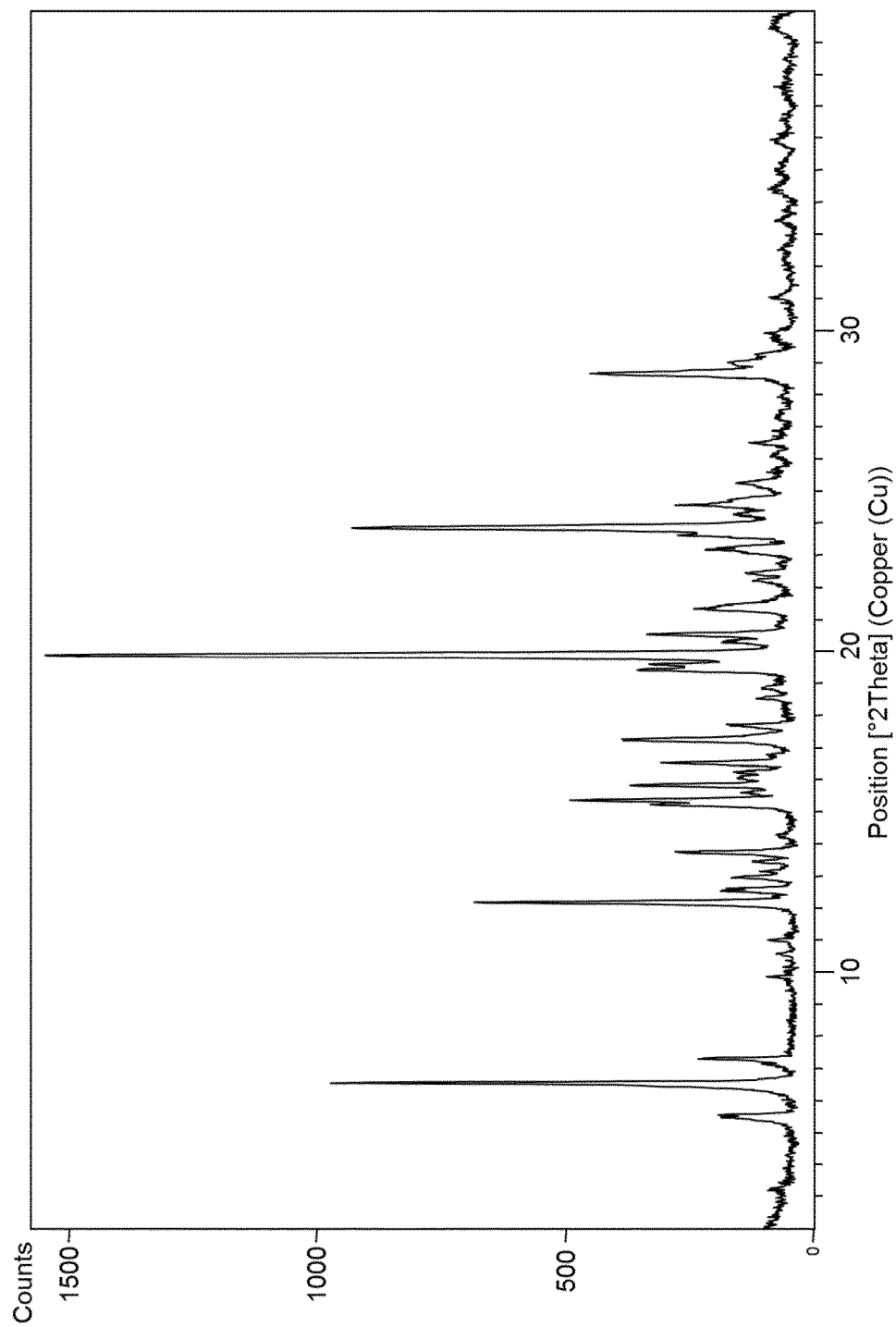
FIG. 3: XRPD of 1-(β-D-glucopyranosyl)-4-methyl-3-[5-(4-fluorophenyl)-2-thienylmethyl]benzene hydrate form HxB

The X-ray powder diffractogram of form HxB comprises additional characteristic peaks at 2-theta angles of 5.6±0.2°, 12.6±0.2°, 13.7±0.2°, 15.2±0.2°, 15.8±0.2°, 16.5±0.2°, 17.3±0.2°, 19.4±0.2°, 19.6±0.2°, 20.5±0.2°, 21.3±0.2°, 23.6±0.2°, 24.6±0.2° and 28.7±0.2°. A representative diffractogram is displayed in FIG. 3. Therefore, in one embodiment, the present invention relates to a crystalline form of a non-stoichiometric hydrate of 1-(β-D-glucopyranosyl)-4-methyl-3-[5-(4-fluorophenyl)-2-thienylmethyl]benzene which has an X-ray powder diffraction pattern substantially the same as the X-ray powder diffraction pattern shown in FIG. 3 when measured using CuKα radiation.

Figure 4:
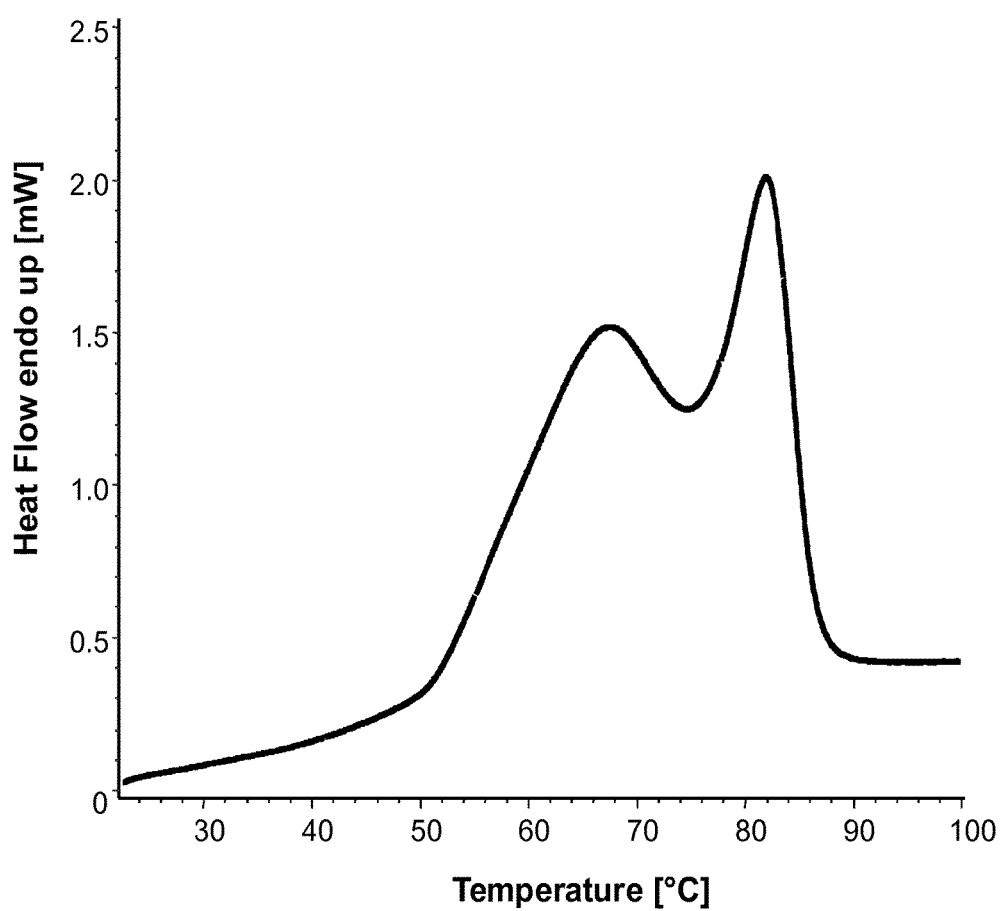
FIG. 4: DSC curve of 1-(β-D-glucopyranosyl)-4-methyl-3-[5-(4-fluorophenyl)-2-thienylmethyl]benzene hydrate form HxB

Moreover, form HxB can be characterized by a melting point having a peak maximum at about 82° C. determined by DSC at a heating rate of 5° C./min. A representative DSC thermogram is displayed in FIG. 4.

Form HxB is a crystalline non-stoichiometric hydrate comprising a water content in the range of about 6.4 to 8.0%. For example, form HxB has a water content of about 6.4% at a RH of about 40% and a water content of about 8.0% at a RH of about 95% as determined by gravimetric moisture sorption/desorption and TGA.

In a second aspect, the present invention relates to processes for the preparation of a crystalline form of a non-stoichiometric hydrate of 1-(β-D-glucopyranosyl)-4-methyl-3-[5-(4-fluorophenyl)-2-thienylmethyl]benzene comprising the steps of:
(a) forming a suspension of amorphous 1-(β-D-glucopyranosyl)-4-methyl-3-[5-(4-fluorophenyl)-2-thienylmethyl]benzene in water;
(b) subjecting the obtained suspension to a particle size reduction process; and
(c) isolating the obtained crystals.

1-(β-D-glucopyranosyl)-4-methyl-3-[5-(4-fluorophenyl)-2-thienylmethyl]benzene is applied as a non-crystalline starting material, for example as an oily or solid amorphous material, which can be prepared in accordance with the procedures described in WO 2005/012326 A1. It is essential that the oily or solid amorphous 1-(β-D-glucopyranosyl)-4-methyl-3-[5-(4-fluorophenyl)-2-thienylmethyl]benzene starting material is free of crystalline 1-(β-D-glucopyranosyl)-4-methyl-3-[5-(4-fluorophenyl)-2-thienylmethyl]benzene hemihydrate, as seed crystals of the hemihydrate prevent the building of the non-stoichiometric hydrates HxA and HxB. On the other hand, the chemical purity of the starting material is not critical with respect to the crystallization of the hydrates HxA and HxB as these forms can also be obtained from relatively impure 1-(β-D-glucopyranosyl)-4-methyl-3-[5-(4-fluorophenyl)-2-thienylmethyl]benzene starting material according to the processes of the present invention.

In a first step, 1-(β-D-glucopyranosyl)-4-methyl-3-[5-(4-fluorophenyl)-2-thienylmethyl]benzene is suspended in water at a concentration ranging from 2 to 100 g/L, preferably from 4 to 50 g/L, more preferably from 8 to 25 g/L and most preferably at a concentration of about 10 g/L. The temperature of the obtained suspension preferably ranges from 1 to 60° C., most preferably the suspension is kept at about room temperature.

The thus obtained suspension mainly consists of coarse agglomerated amorphous 1-(β-D-glucopyranosyl)-4-methyl-3-[5-(4-fluorophenyl)-2-thienylmethyl]benzene particles, which have limited solvent contact resulting in long solvent-mediated solid state transformation times. In order to achieve a fast and reliable solvent-mediated solid state transformation from amorphous to crystalline 1-(β-D-glucopyranosyl)-4-methyl-3-[5-(4-fluorophenyl)-2-thienylmethyl]benzene it is crucial that the solid material is well dispersed in water to ensure sufficient solvent contact. This can be achieved by a particle size reduction process, for example a mechanical particle size reduction process such as magnetic stirring, sonomilling or wet milling/grinding.

Usually magnetic stirring is only applied on small scales such as volumes of ≤1 L. On larger scales, such as volumes of >1 L overhead stirring is preferred and in these cases sonomilling and wet milling/grinding are the preferred mechanical particles size reduction processes.

Mechanical particle size reduction by sonomilling may be performed by subjecting the aqueous suspension of 1-(β-D-glucopyranosyl)-4-methyl-3-[5-(4-fluorophenyl)-2-thienylmethyl]benzene to an ultrasonic power input ranging from 10 to 100 W, more preferably from 20 to 80 W and most preferably from 40 to 60 W for a time preferably ranging from 5 to 60 min, more preferably from 10 to 40 min and most preferably from 15 to 20 min. The ultrasonic treatment may be performed batchwise either in an ultrasonic bath or in a vessel fitted with a submersible ultrasonic generator or as a continuous flow process through an ultrasonic cell.

Wet milling/grinding can be performed using a shearing machine such as a high-speed rotor-stator device or high shear mill either by placing the shearing machine in the reactor containing the aqueous 1-(β-D-glucopyranosyl)-4-methyl-3-[5-(4-fluorophenyl)-2-thienylmethyl]benzene suspension or by continuously passing the aqueous suspension through the shearing machine.

The temperature of the aqueous 1-(β-D-glucopyranosyl)-4-methyl-3-[5-(4-fluorophenyl)-2-thienylmethyl]benzene suspension is preferably kept at ≤60° C., more preferably at ≤50° C. and most preferably at ≤40° C. during the mechanical particle size reduction process.

After the mechanical particle size reduction process is complete, a stir-out period, preferably lasting for 1 to 48 h, more preferably for 2 to 24 h and most preferably for 4 to 12 h, is applied. During the stir-out period a temperature of ≤60° C., preferably of ≤50° C., more preferably of ≤40° C. and most preferably of about room temperature is applied.

Finally, the obtained crystals are collected by any conventional method such as filtration or centrifugation, most preferably by filtration.

Then the crystals are optionally dried at temperatures ranging from 25 to 60° C., more preferably from 25 to 50° C. and most preferably from 25 to 40° C. for a time preferably ranging from 6 to 72 h, more preferably from 12 to 48 h and most preferably from 18 to 24 h. Drying may be performed under vacuum or at ambient pressure. Preferably drying is performed under vacuum such as ≤100 mbar, more preferably ≤50 mbar and most preferably ≤30 mbar.

In order to obtain crystalline form HxA, the solid material is then subjected to an atmosphere having a relative humidity of ≤30% at about room temperature for a time preferably ranging from 6 h to 1 month, more preferably from 12 h to 1 week and most preferably from 24 to 48 h.

In contrast, crystalline form HxB of 1-(β-D-glucopyranosyl)-4-methyl-3-[5-(4-fluorophenyl)-2-thienylmethyl]benzene can be obtained by subjecting the solid material to an atmosphere preferably having a RH of ≥45% at about room temperature, more preferably of ≥60% at about room temperature and most preferably of ≥80% at about room temperature for a time preferably ranging from 6 h to 1 month, more preferably from 12 h to 1 week and most preferably from 24 to 48 h.

The crystalline forms HxA and HxB of 1-(β-D-glucopyranosyl)-4-methyl-3-[5-(4-fluorophenyl)-2-thienylmethyl]benzene are obtained in high yield, for example ≥90%, more preferably 95% of theory according to the processes of the present invention.

WO 2008/069327 A1 discloses methods for preparing crystalline 1-(β-D-glucopyranosyl)-4-methyl-3-[5-(4-fluorophenyl)-2-thienylmethyl]benzene hemihydrate by precipitation or recrystallization from a solvent mixture comprising a good organic solvent, water and optionally a poor organic solvent. In example 1 of said patent application the hemihydrate is crystallized from ethyl acetate, diethyl ether and water, whereas in example 2 of the same application acetone/water is used as a crystallization medium. Example 9 of WO 2009/035969 A1 and example 14 of WO 2010/043682 A2 both disclose crystallization processes for the preparation of 1-(β-D-glucopyranosyl)-4-methyl-3-[5-(4-fluorophenyl)-2-thienylmethyl]benzene hemihydrate from a mixture of ethyl acetate, water and n-heptane. In example 1 of WO 2011/003976 A1 the crystallization of 1-(β-D-glucopyranosyl)-4-methyl-3-[5-(4-fluorophenyl)-2-thienylmethyl]benzene hemihydrate is performed from a mixture of isopropyl acetate and water and example 11 of WO 2011/047113 A1 describes the crystallization of 1-(β-D-glucopyranosyl)-4-methyl-3-[5-(4-fluorophenyl)-2-thienylmethyl] benzene hemihydrate from a methanol/water mixture.

However, the use of organic solvents and organic antisolvents in crystallization processes is associated with certain drawbacks since organic solvents and organic antisolvents are usually expensive, toxic and/or harmful to health and/or the environment. In addition, residual organic solvents are often not completely removed from active pharmaceutical ingredients by practical manufacturing techniques. Nevertheless, they should be decreased to a minimum amount as these residual solvents show no therapeutic effect and are mostly toxic. Therefore, an environmentally friendly crystallization process for the preparation of crystalline 1-(β-D-glucopyranosyl)-4-methyl-3-[5-(4-fluorophenyl)-2-thienylmethyl]benzene, free of organic solvents and organic antisolvents, and consequently a crystalline from of 1-(β-D-glucopyranosyl)-4-methyl-3-[5-(4-fluorophenyl)-2-thienylmethyl]benzene obtained from this environmentally friendly crystallization process, lacking residual organic solvents, is highly desirable.

The inventors of the present invention found novel crystalline hydrates of 1-(β-D-glucopyranosyl)-4-methyl-3-[5-(4-fluorophenyl)-2-thienylmethyl]benzene which can be prepared from water alone without the need of organic solvents. This is surprising because the prior art literature suggests that an organic solvent is a prerequisite for obtaining crystals of 1-(β-D-glucopyranosyl)-4-methyl-3-[5-(4-fluorophenyl)-2-thienylmethyl]benzene. In fact, the crystalline hydrates prepared according to the second aspect of the present invention are free of any residual organic solvents due to the organic solvent free production processes. This is regarded as a significant advantage compared to previous forms of this API. In addition the production processes of the novel crystalline hydrates are cheap, safe and environmentally friendly.

In a third aspect, the present invention relates to an economical and industrially applicable process for the preparation of a crystalline form of a non-stoichiometric hydrate of the compound of formula (I) (1-(β-D-glucopyranosyl)-4-methyl-3-[5-(4-fluorophenyl)-2-thienyl-methyl] benzene) comprising the steps of:
(i) forming a suspension (U) comprising water and seed crystals of the compound of formula (I),
(ii) forming a solution (O) comprising a water-miscible organic solvent and the compound of formula (I),
(iii) forming a mixture (M) comprising not more than 13 volume % of a water-miscible organic solvent by combining solution (O) and suspension (U) and
(iv) crystallizing the compound of formula (I).

The seed crystals used in step (i) of the process can be obtained, for example, by following the process of the second aspect described above.

In a specifically preferred embodiment, the present invention relates to an economical and industrially applicable process for the preparation of a crystalline form of a non-stoichiometric hydrate of the compound of formula (I) (1-(β-D-glucopyranosyl)-4-methyl-3-[5-(4-fluorophenyl)-2-thienyl-methyl]benzene) comprising the steps of:
(i) forming a suspension (U) comprising water and seed crystals of the compound of formula (I),
(ii) forming a solution (O) comprising a water-miscible organic solvent and the compound of formula (I),
(iii) forming a mixture (M) comprising not more than 13 volume % of a water-miscible organic solvent by combining solution (O) and suspension (U) and
(iv) crystallizing the compound of formula (I),
wherein the seed crystals are characterized by a X-ray powder diffractogram comprising characteristic peaks at 2-Theta angles of 5.4±0.2°, 6.7±0.2°, 13.2±0.2°, 16.1±0.2°, 19.6±0.2° and 24.1±0.2° and/or 6.6±0.2°, 7.3±0.2°, 12.2±0.2°, 15.4±0.2°, 19.9±0.2° and 23.9±0.2° when measured at room temperature using Cu-Kα radiation having a wavelength of 0.15419 nm.

Suspension (U) of the present process comprises water and a crystalline seed of 1-(β-D-glucopyranosyl)-4-methyl-3-[5-(4-fluorophenyl)-2-thienylmethyl]benzene. The seed crystals are selected from form HxA, form HxB or mixtures thereof, whereat form Hy0.5 should not be applied for the preparation of the suspension as this form triggers the building of form Hy0.5. The aqueous suspension is prepared by adding form HxA and/or form HxB seeds to water or vice versa. Preferably, the suspension is prepared at room temperature and the amount of seed crystals is chosen such that they don't dissolve completely. In order to avoid complete dissolution the seed crystals are preferably applied in an amount of about ≥0.05 g per liter water, e.g. about 0.1 g, 0.5 g or 1.0 g seed crystals per liter water are applied. The suspension preferably comprises 0.5 to 10 weight %, more preferably 0.5 to 5 weight % and most preferably 0.5 to 2.5 weight % seed crystals referred to the amount of 1-(β-D-glucopyranosyl)-4-methyl-3-[5-(4-fluorophenyl)-2-thienylmethyl]benzene employed for the preparation of solution (O).

Form HxA and/or form HxB seed crystals can be prepared, as described above in the second aspect of the present invention, by suspending non-crystalline 1-(β-D-glucopyranosyl)-4-methyl-3-[5-(4-fluorophenyl)-2-thienylmethyl] benzene, for example in form of an oil, a gum, a resin or an amorphous solid (for example prepared in a similar manner as disclosed in Example 1 of WO 2005/012326 A1 or according to Example 13 herein), in water and applying mechanical stress such as magnetic stirring, sonomilling or wet milling/grinding to the obtained suspension. The thus obtained crystals can be collected by any conventional method such as filtration or centrifugation, preferably by filtration. The isolated crystals are thereafter dried at a temperature of about 25 to 60° C. preferably under vacuum such as about 20 to 100 mbar. A concrete example for the preparation of the seed crystals is e.g. provided in Example 1 herein.

Mixtures of form HxA and form HxB can be obtained by subjecting form HxB crystals to an atmosphere preferably having a relative humidity of <30% at about room temperature until equilibrium is reached. Alternatively, mixtures of form HxA and form HxB can be prepared by physically mixing form HxA and form HxB crystals in a closed containment and keeping the final blend preferably at a relative humidity of <30% at about room temperature.

Solution (O) of the present process comprises a water-miscible organic solvent and 1-(β-D-glucopyranosyl)-4-methyl-3-[5-(4-fluorophenyl)-2-thienylmethyl]benzene. Any form of 1-(β-D-glucopyranosyl)-4-methyl-3-[5-(4-fluorophenyl)-2-thienylmethyl]benzene can be used for the preparation of the solution e.g. crystalline, amorphous or mixtures of crystalline and amorphous 1-(β-D-glucopyranosyl)-4-methyl-3-[5-(4-fluorophenyl)-2-thienylmethyl]benzene can be applied as starting material. Suitable crystalline forms which can be employed for the preparation of the solution are for example form Hy0.5, form HxA, form HxB or mixtures thereof. 1-(β-D-glucopyranosyl)-4-methyl-3-[5-(4-fluorophenyl)-2-thienylmethyl]benzene is dissolved in a suitable water-miscible organic solvent, wherein the final solution comprises about 80 to 350 g, preferably about 150 to 350 g, more preferably about 200 to 350 g and most preferably about 300 to 350 g 1-(β-D-glucopyranosyl)-4-methyl-3-[5-(4-fluorophenyl)-2-thienylmethyl]benzene per liter water-miscible organic solvent. The solution is preferably prepared at a temperature of about 15 to 60° C., more preferably of about 20 to 40° C. and most preferably the solution is prepared at room temperature. The obtained solution may optionally be filtered in order to remove any undissolved particles. Optionally, the solution is treated with charcoal before filtration.

Suitable water-miscible organic solvents which can be used for the preparation of solution (O) are preferably selected from water-miscible alcohols, water-miscible ketones, water-miscible cyclic ethers or mixtures thereof, whereat water-miscible alcohols are most preferred. Suitable water-miscible alcohols are for example methanol, ethanol, n-propanol, isopropanol or mixtures thereof, whereat ethanol is the most preferred alcohol. Examples for suitable water-miscible ketones are acetone, methylethyl ketone or mixtures thereof, whereat acetone is the most preferred ketone. Suitable water-miscible cyclic ethers are for example selected from tetrahydrofuran, methyltetrahydrofuran, 1,4-dioxane or mixtures thereof, whereat tetrahydrofuran is the most preferred cyclic ether. Most preferably ethanol is used as solvent for the preparation of the solution.

In a next step a mixture (M) comprising not more than about 13 volume % of a water-miscible organic solvent is prepared by combining solution (O) and suspension (U). The low water-miscible organic solvent concentration of the obtained mixture prevents the nucleation and subsequent crystallization of form Hy0.5 and therefore ensures the reliable receipt of the non-stoichiometric hydrates form HxA and/or form HxB. The stoichiometric hydrate form Hy0.5 is at least partially obtained when the water-miscible organic solvent concentration of the mixture increases the critical value of about 13 volume %. For example when about 14.6 volume % of a water-miscible organic solvent were present in the mixture form Hy0.5 was obtained, whereas a water-miscible organic solvent concentration of about 2.9 to 13.0 volume % was found to prohibit the building of form Hy0.5 (see also Examples 7a-7f herein).

Preferably, mixture (M) is prepared by adding solution (O) comprising a water-miscible organic solvent and 1-(β-D-glucopyranosyl)-4-methyl-3-[5-(4-fluorophenyl)-2-thienylmethyl]benzene to suspension (U) comprising water and form HxA and/or form HxB seed crystals. The solution is added to the aqueous seed crystal suspension in a manner suitable for preventing the nucleation and subsequent crystallization of form Hy0.5. For example, the mixture is prepared by charging a reactor with the aqueous seed crystal suspension and adding solution (O) to suspension (U) under thorough stirring and at such an addition rate that the water-miscible organic solvent concentration in the mixing zone of the obtained mixture (M) does not exceed about 13 volume % until the addition is complete (see also Example 10 herein).

Preferably, the crystallization of Form Hy0.5 is prohibited by keeping the temperature of mixture (M) at about 0 to 15° C. until the addition of solution (O) to suspension (U) is complete. In this case the agitation speed and the addition rate are not critical with regards to the crystallization of the wrong solid form. For example, the temperature of the aqueous seed crystal suspension is preferably cooled to about 0 to 15° C., more preferably to about 0 to 10° C. and most preferably to about 0 to 5° C. prior to the addition of the solution. In addition, the temperature of the solution is preferably decreased to about −10 to 10° C., more preferably to about −5 to 5° C. and most preferably to about 0 to 5° C. prior to the addition. Then the cold solution is added to the cold aqueous seed crystal suspension, whereat the temperature of the obtained mixture is kept at about 0 to 15° C. until the addition is complete.

Most preferably, the crystallization of form Hy0.5 is prevented by ensuring that the water-miscible organic solvent concentration in the mixing zone of mixture (M) does not exceed about 13 volume % and the temperature of the mixture is kept at about 0 to 15° C. until the addition of solution (O) to suspension (U) is complete.

Alternatively, instead of adding solution (O) comprising a water-miscible organic solvent and 1-(β-D-glucopyranosyl)-4-methyl-3-[5-(4-fluorophenyl)-2-thienylmethyl]benzene to suspension (U) comprising water and form HxA and/or form HxB seed crystals the mixture can be prepared by performing the addition vice versa. In this case it is a prerequisite to keep the temperature of mixture (M) at about 0 to 15° C. until the addition is complete in order to avoid the crystallization of form Hy0.5. Again the aqueous seed crystal suspension is cooled to a temperature of about 0 to 15° C., more preferably of about 0 to 10° C. and most preferably of about 0 to 5° C. prior to the addition. Furthermore, the temperature of the solution is precooled to about −10 to 10° C., more preferably to about −5 to 5° C. and most preferably to about 0 to 5° C. Then the cold aqueous seed crystal suspension is added to the precooled solution under thorough stirring, whereat the temperature of the obtained mixture (M) is kept at about 0 to 15° C. until the addition is complete.

Once solution (O) and the aqueous seed crystal suspension (U) have been combined, the obtained mixture (M) is preferably kept at a temperature of about 20 to 45° C., more preferably at a temperature of about 25 to 40° C. in order to initiate crystallization. Mixture (M), which comprises not more than about 13 volume % of a water-miscible organic solvent, may be kept at the applied temperature, preferably under stirring, for about 1 to 72 hours, more preferably for about 2 to 48 hours and most preferably for about 4 to 24 hours, in order to ensure complete crystallization and ripening of the crystals.

Thereafter, the obtained crystals may be isolated by any conventional method such as filtration or centrifugation, most preferably the crystals are collected by filtration.

The isolated crystals may then be dried preferably at a temperature of about ≤70° C., more preferably of about ≤60° C. and most preferably of about ≤50° C. such as a temperature of about 25 to 40° C. Drying can be performed under vacuum or at ambient pressure. Preferably drying is performed by applying a vacuum of about ≤100 mbar, more preferably of about ≤50 mbar and most preferably of about ≤30 mbar. The crystals are preferably dried for about 6 to 72 hours, more preferably for about 12 to 48 hours and most preferably for about 18 to 24 hours at the applied conditions.

Finally, the dried crystals may be subjected to different relative humidities at room temperature until equilibrium is reached, whereupon, depending on the selected relative humidity, form HxA or form HxB is obtained. For example form HxA is obtained by subjecting the dried crystals to an atmosphere preferably having a relative humidity of ≤30% at about room temperature until equilibrium is reached. In contrast, form HxB is obtained by subjecting the dried crystals to an atmosphere preferably having a relative humidity of ≥45%, at about room temperature, more preferably of ≥60% at about room temperature and most preferably of ≥80% at about room temperature until equilibrium is reached. Equilibrium is reached when the crystals subjected to certain relative humidities at room temperature do neither gain nor lose moisture anymore.

Mixtures of form HxA and form HxB can be obtained by subjecting form HxB crystals to an atmosphere preferably having a relative humidity of <30% at about room temperature until equilibrium is reached. Alternatively, mixtures of form HxA and form HxB can be prepared by physically mixing form HxA and form HxB crystals in a closed containment and keeping the final blend preferably at a relative humidity of <30% at about room temperature.

The form HxA and/or form HxB crystals prepared according to the process of the third aspect of the present invention are lath-shaped preferably having a length of about 10 to 100 μm, more preferably of about 30 to 100 μm and most preferably of about 50 to 100 μm. Compared to the crystals obtained from the process of the second aspect of the present invention, which comprises a mechanical particle size reduction step, the crystals obtained from the process of the third aspect of the present invention show a significant increase in particle sizes, leading to better isolation properties such as shorter filtration times. Short filtration times are desirable especially on industrial scale, because this renders a production process more economic.

The novel crystalline non-stoichiometric hydrates HxA and HxB of the present invention show favorable physicochemical properties. For example, they are chemically stable, have favorable crystal habits and therefore show good handling properties such as good isolation, drying, flow and compaction properties. When HxA and HxB are prepared according to the process described in the third aspect of the present invention, the handling properties are further improved as more favorable particle sizes and crystal shapes are obtained.

Figure 7:
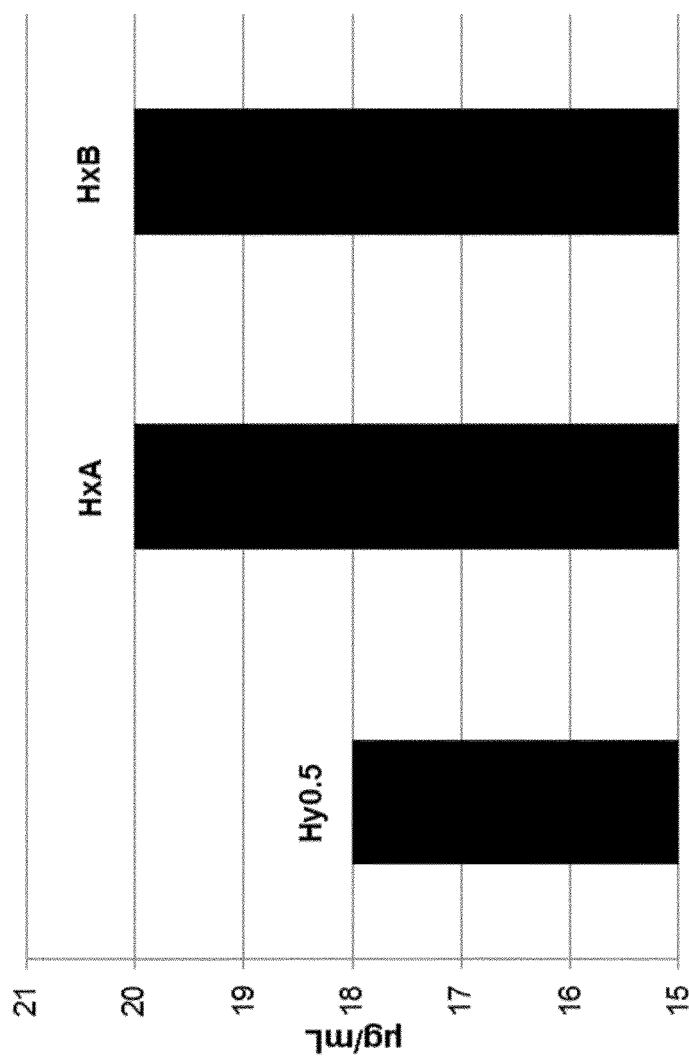
FIG. 7: Aqueous solubilities of 1-(β-D-glucopyranosyl)-4-methyl-3-[5-(4-fluorophenyl)-2-thienylmethyl]benzene forms HxA and HxB of the present invention and 1-(β-D-glucopyranosyl)-4-methyl-3-[5-(4-fluorophenyl)-2-thienylmethyl]benzene hemihydrate of WO 2008/069327 A1 (form Hy0.5) at 25.0±1.0° C.

Furthermore, the bioavailability of a compound intended to be administered orally is dependent on the compound's solubility as well as the compound's permeability, according to the Biopharmaceutical Classification System (BCS). Therefore, a crystalline form of 1-(β-D-glucopyranosyl)-4-methyl-3-[5-(4-fluorophenyl)-2-thienylmethyl]benzene having increased solubility and consequently increased oral bioavailability is desirable. The aqueous solubilities of the different crystalline forms of 1-(β-D-glucopyranosyl)-4-methyl-3-[5-(4-fluorophenyl)-2-thienylmethyl]benzene at $25.0 \pm 1.0°$ C. have been determined (see example 5 and FIG. 7 of the present invention). Surprisingly, the novel crystalline non-stoichiometric hydrates HxA and HxB of 1-(β-D-glucopyranosyl)-4-methyl-3-[5-(4-fluorophenyl)-2-thienylmethyl]benzene of the present invention both show a 10% increased solubility in water compared to the crystalline 1-(β-D-glucopyranosyl)-4-methyl-3-[5-(4-fluorophenyl)-2-thienylmethyl]benzene hemihydrate of WO 2008/069327 A1. Hence crystalline forms HxA and HxB are preferred for the preparation of an orally administered medicament since, according to the BCS, the oral bioavailabilities of the crystalline non-stoichiometric hydrates of the present invention are higher than that for the crystalline hemihydrate of WO 2008/069327 A1.

Therefore, in a fourth aspect, the present invention relates to a pharmaceutical composition comprising an effective amount of a crystalline form of a non-stoichiometric hydrate of 1-(β-D-glucopyranosyl)-4-methyl-3-[5-(4-fluorophenyl)-2-thienylmethyl]benzene and a pharmaceutically acceptable carrier.

As used herein, the term "pharmaceutically acceptable carrier" includes any and all suitable solvents, dispersion media, coatings, surfactants, antioxidants, preservatives (for example, antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The pharmaceutical compositions of the present invention comprising an effective amount of a crystalline form of a non-stoichiometric hydrate of 1-(β-D-glucopyranosyl)-4-methyl-3-[5-(4-fluorophenyl)-2-thienylmethyl]benzene and a pharmaceutically acceptable carrier are preferably packaged or filled into containers. Containers are typically used for stable storage of the pharmaceutical compositions of the present invention, for example at a temperature of 20° C. to 30° C. e.g. at about 25° C. for a prolonged time, for example, for at least 6 months, preferably at least 24 months, for up to at least about 30 months, or for up to about 60 months.

In one embodiment, the container used for the stable storage of the pharmaceutical compositions of the present invention comprising crystalline 1-(β-D-glucopyranosyl)-4-methyl-3-[5-(4-fluorophenyl)-2-thienylmethyl]benzene in the form of the non-stoichiometric hydrate HxA ensures an environment having a relative humidity of ≤30%.

In one embodiment, the container used for the stable storage of the pharmaceutical compositions of the present invention comprising crystalline 1-(β-D-glucopyranosyl)-4-methyl-3-[5-(4-fluorophenyl)-2-thienylmethyl]benzene in the form of the non-stoichiometric hydrate HxB ensures an environment having a relative humidity of ≥40%.

A preferred container is a bottle, in particular a polyethylene bottle, for example a HDPE bottle or a glass bottle, having for example a screw closure with an aluminum induction seal liner, or is a blister, for example an aluminum blister or strip, for example a blister consisting of two aluminum foils or strips, or may be any other suitable container. More preferably said container is a gas-tight container, such as an air-tight container.

In a fifth aspect, the present invention relates to a crystalline form of a non-stoichiometric hydrate of 1-(β-D-glucopyranosyl)-4-methyl-3-[5-(4-fluorophenyl)-2-thienylmethyl]benzene for use as a medicament. In one embodiment, the invention relates to a crystalline form of a non-stoichiometric hydrate of 1-(β-D-glucopyranosyl)-4-methyl-3-[5-(4-fluorophenyl)-2-thienylmethyl]benzene for use in the treatment of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis and/or hypertension. In one embodiment, the crystalline form of a non-stoichiometric hydrate of 1-(β-D-glucopyranosyl)-4-methyl-3-[5-(4-fluorophenyl)-2-thienylmethyl]benzene is form HxA. In another embodiment, the crystalline form of a non-stoichiometric hydrate of 1-(β-D-glucopyranosyl)-4-methyl-3-[5-(4-fluorophenyl)-2-thienylmethyl]benzene is form HxB.

In one embodiment, the present invention relates to a method for the treatment of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis and/or hypertension which comprises administering a therapeutically effective amount of a crystalline form of a non-stoichiometric hydrate of 1-(β-D-glucopyranosyl)-4-methyl-3-[5-(4-fluorophenyl)-2-thienylmethyl]benzene to a subject in need thereof. In one embodiment, the crystalline form of a non-stoichiometric hydrate of 1-(β-D-glucopyranosyl)-4-methyl-3-[5-(4-fluorophenyl)-2-thienylmethyl]benzene is form HxA. In another embodiment, the crystalline form of a non-stoichiometric hydrate of 1-(β-D-glucopyranosyl)-4-methyl-3-[5-(4-fluorophenyl)-2-thienylmethyl]benzene is form HxB.

In one embodiment, the invention relates to the use of a crystalline form of a non-stoichiometric hydrate of 1-(β-D-glucopyranosyl)-4-methyl-3-[5-(4-fluorophenyl)-2-thienylmethyl]benzene as an active pharmaceutical ingredient in a medicament. In another embodiment, the invention relates to the use of a crystalline form of a non-stoichiometric hydrate of 1-(β-D-glucopyranosyl)-4-methyl-3-[5-(4-fluorophenyl)-2-thienylmethyl]benzene as an active pharmaceutical ingredient in a medicament for the treatment of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis and/or hypertension. In one embodiment, the crystalline form of a non-stoichiometric hydrate of 1-(β-D-glucopyranosyl)-4-methyl-3-[5-(4-fluorophenyl)-2-thienylmethyl]benzene is form HxA. In another embodiment, the crystalline form of a non-stoichiometric hydrate of 1-(β-D-glucopyranosyl)-4-methyl-3-[5-(4-fluorophenyl)-2-thienylmethyl]benzene is form HxB.

In one embodiment, the invention relates to the use of a crystalline form of a non-stoichiometric hydrate of 1-(β-D-glucopyranosyl)-4-methyl-3-[5-(4-fluorophenyl)-2-thienylmethyl]benzene for the manufacture of a medicament for the treatment of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis and/or hypertension. In one embodiment, the crystalline form of a non-stoichiometric hydrate of 1-(β-D-glucopyranosyl)-4-methyl-3-[5-(4-fluorophenyl)-2-thienylmethyl]benzene is form HxA. In another embodiment, the crystalline form of a non-stoichiometric hydrate of 1-(β-D-glucopyranosyl)-4-methyl-3-[5-(4-fluorophenyl)-2-thienylmethyl]benzene is form HxB.

A crystalline form of a non-stoichiometric hydrate of 1-(β-D-glucopyranosyl)-4-methyl-3-[5-(4-fluorophenyl)-2-thienylmethyl]benzene can be administered alone or in combination with other pharmaceutically active compounds such as further antidiabetic agents. In this case a crystalline form of a non-stoichiometric hydrate of 1-(β-D-glucopyranosyl)-4-methyl-3-[5-(4-fluorophenyl)-2-thienylmethyl]benzene and the additional antidiabetic agent can be administered either simultaneously or sequentially. For example a crystalline form of a non-stoichiometric hydrate of 1-(β-D-glucopyranosyl)-4-methyl-3-[5-(4-fluorophenyl)-2-thienylmethyl]benzene may be administered in combination with metformin, sulfonylurea, pioglitazone, insulin or mixtures thereof, most preferably in combination with metformin.

Therefore, in a sixth aspect, the present invention relates to a pharmaceutical combination comprising an effective amount of a crystalline form of a non-stoichiometric hydrate of 1-(β-D-glucopyranosyl)-4-methyl-3-[5-(4-fluorophenyl)-2-thienylmethyl]benzene and metformin. In one embodiment, the crystalline form is form HxA. In another embodiment, the crystalline form is form HxB. In one embodiment, the pharmaceutical combination comprises a crystalline form of a non-stoichiometric hydrate of 1-(β-D-glucopyranosyl)-4-methyl-3-[5-(4-fluorophenyl)-2-thienylmethyl]benzene, for example form HxA or HxB, and metformin within a single unit dose pharmaceutical composition comprising a pharmaceutically acceptable carrier.

EXAMPLES

The X-ray powder diffractograms (XRPDs) were obtained with an X'Pert PRO diffractometer (PANalytical, Almelo, The Netherlands) equipped with a theta/theta coupled goniometer in transmission geometry, programmable XYZ stage with well plate holder, Cu-Kα1,2 radiation source (wavelength 0.15419 nm) with a focussing mirror, a 0.5° divergence slit, a 0.02° soller slit collimator and a 0.5° anti-scattering slit on the incident beam side, a 2 mm anti-scattering slit, a 0.02° soller slit collimator, a Ni-filter and a solid state PIXcel detector on the diffracted beam side. The patterns were recorded at a tube voltage of 40 kV, tube current of 40 mA, applying a stepsize of 0.013° 2-Theta with 40 sec per step in the angular range of 2° to 40° 2-Theta. A typical precision of the 2-Theta values is in the range of ±0.2° 2-Theta. Thus a diffraction peak that appears at 5.0° 2-Theta can appear between 4.8 and 5.2° 2-Theta on most X-ray diffractometers under standard conditions.

Differential scanning calorimetry (DSC) was performed with a Diamond-DSC (Perkin-Elmer, Norwalk, Conn., USA) using Pyris 2.0 software. Approximately 2 to 5±0.0005 mg sample (using a UM3 ultramicrobalance, Mettler, Greifensee, CH) was weighed into an Al-pan (25 μl) and sealed with a cover, which was perforated by a needle. Dry nitrogen was used as the purge gas (purge: 20 mL/min).

The water values at varying relative humidities were obtained by recording moisture sorption isotherms with a SPS-11 moisture sorption analyzer (MD Messtechnik, Ulm, D). The measurement cycle was started at 30% relative humidity (RH), decreased in 10% steps down to 0% RH, increased up to 90% RH in 10% steps, decreased in 10% steps down to 0% RH and finally increased in 1 step up to 43% RH to determine subsequently the absolute water content by TGA analysis. The equilibrium condition for each step was set to a mass constancy of ±0.005% over 60 min. The temperature was 25±0.1° C.

Thermogravimetric analysis (TGA) was performed using the following equipment/conditions: Thermogravimetric-system TGA-7, Pyris-Software für Windows NT, (Perkin-Elmer, Norwalk, Conn., USA), Platinum-sample holder (50 μl), Nitrogen as the purge gas (Sample purge: 20 mL/min, balance purge: 40 mL/min). Heating rate: 10 K/min; Heating Range: 25-100° C.;

Example 1

Preparation of 1-(β-D-glucopyranosyl)-4-methyl-3-[5-(4-fluorophenyl)-2-thienylmethyl]benzene form HxA via magnetic stirring A suspension of 5.0 g amorphous 1-(β-D-glucopyranosyl)-4-methyl-3-[5-(4-fluorophenyl)-2-thienylmethyl]benzene (for example prepared in accordance with the procedures described in WO 2005/012326 A1) in 500 mL water was stirred at room temperature for 18 hours using a magnetic stirrer. Thereafter the solid material was collected by filtration and dried at 40° C. under vacuum (≤30 mbar) for about 24 hours (<30% relative humidity) to obtain 4.8 g (96% of theory) of 1-(β-D-glucopyranosyl)-4-methyl-3-[5-(4-fluorophenyl)-2-thienylmethyl]benzene form HxA.

Example 2

Preparation of 1-(β-D-glucopyranosyl)-4-methyl-3-[5-(4-fluorophenyl)-2-thienylmethyl]benzene form HxA via sonomilling A suspension of 5.0 g amorphous 1-(β-D-glucopyranosyl)-4-methyl-3-[5-(4-fluorophenyl)-2-thienylmethyl]benzene (for example prepared in accordance with the procedures described in WO 2005/012326 A1) in 500 mL water was stirred at 25° C. for 2 h using an overhead stirrer. Then the suspension was sonicated at 60 W for 20 min (Prosonix, Sonolab™) and further stirred at 25° C. overnight. The obtained crystals were collected by filtration and dried at 40° C. under vacuum (≤40 mbar) for 24 hours (<30% relative humidity), whereat form HxA of 1-(β-D-glucopyranosyl)-4-methyl-3-[5-(4-fluorophenyl)-2-thienylmethyl]benzene was obtained.

Example 3

Preparation of 1-(β-D-glucopyranosyl)-4-methyl-3-[5-(4-fluorophenyl)-2-thienylmethyl]benzene form HxB via magnetic stirring A suspension of 0.50 g amorphous 1-(β-D-glucopyranosyl)-4-methyl-3-[5-(4-fluorophenyl)-2-thienylmethyl]benzene (for example prepared in accordance with the procedures described in WO 2005/012326 A1) in 50 mL water was stirred at room temperature for 6 hours using a magnetic stirrer. Thereafter the solid material was collected by filtration, dried overnight at 40° C. under vacuum (≤30 mbar) and subsequently open stored overnight in a desiccator over a saturated ammonium chloride solution at 80±5% RH to obtain 0.45 g (90% of theory) of 1-(β-D-glucopyranosyl)-4-methyl-3-[5-(4-fluorophenyl)-2-thienylmethyl]benzene form HxB.

Example 4

Competitive Slurry in Water

A suspension of 50 mg 1-(β-D-glucopyranosyl)-4-methyl-3-[5-(4-fluorophenyl)-2-thienylmethyl]benzene form HxA (for example prepared according to the procedure described in example 1 of the present invention) and 50 mg 1-(β-D-glucopyranosyl)-4-methyl-3-[5-(4-fluorophenyl)-2-thienylmethyl]benzene hemihydrate (for example prepared according to the procedure described in example 1 of WO 2008/069327 A1) in 4 mL water was stirred at moderate velocity using a magnetic stirrer. The temperature during the slurry experiment was first cycled between 7 to 10° C. for 4 days changing the temperature every 2 hours. Thereafter the suspension was cycled in the range of 10 to 30° C. for 9 days changing the temperature every 2 hours. During the whole experiment the ratio of the two hydrates did not change, which was confirmed with XRPD and indicates that form HxA does not transform under the observed conditions.

Example 5

Aqueous Solubility

The aqueous solubilities of 1-(β-D-glucopyranosyl)-4-methyl-3-[5-(4-fluorophenyl)-2-thienylmethyl]benzene forms HxA and HxB of the present invention and the hemihydrate of 1-(β-D-glucopyranosyl)-4-methyl-3-[5-(4-fluorophenyl)-2-thienylmethyl]benzene described in WO 2008/069327 A1 were determined by the equilibrium solubility method. Saturated solutions of 1-(β-D-glucopyranosyl)-4-methyl-3-[5-(4-fluorophenyl)-2-thienylmethyl]benzene, obtained by stirring 50 mg of each crystalline form in 50 mL water were prepared and stirred at 25±1° C. After 60 minutes of stirring, three samples were withdrawn, filtered through 0.45 µm syringe filters and the filtrates were directly analyzed by HPLC.
Column: C18 4.6×150 mm 5 µm
Eluent A: 0.1% formic acid-water solution
Eluent B: 0.1% formic acid-acetonitril solution
Injection vol.: 100 µL
Column Temp.: 25° C.
Wavelength: 220 nm
Pump flow: 1.2 mL/min
Gradient:

| Gradient: | | | | | | | |
|---|---|---|---|---|---|---|---|
| | Time [min] | | | | | | |
| | 0.0 | 20.0 | 22.0 | 22.5 | 25.0 | 25.3 | 30.0 |
| [%] B | 20 | 80 | 80 | 95 | 95 | 20 | 20 |

Using six concentration points of known 1-(β-D-glucopyranosyl)-4-methyl-3-[5-(4-fluorophenyl)-2-thienylmethyl]benzene concentrations a calibration line was fitted by linear regression. Forms HxA and HxB of the present invention were found to have a 10% increased aqueous solubility compared to the crystalline hemihydrate described in WO 2008/069327 A1. The results are summarized in table 1.

TABLE 1

| Equilibrium aqueous solubilities at 25 ± 1° C. | | |
|---|---|---|
| Crystalline Form | Abs. Solubilities [µg/mL] | Rel. Solubilities [%] |
| hemihydrate of WO 2008/069327 A1 (=Hy0.5) | 18 | 90 |
| form HxA of the present invention | 20 | 100 |
| form HxB of the present invention | 20 | 100 |

Example 6

Preparation of 1-(β-D-glucopyranosyl)-4-methyl-3-[5-(4-fluorophenyl)-2-thienylmethyl]benzene form HxA A reactor was charged with 0.26 g 1-(β-D-glucopyranosyl)-4-methyl-3-[5-(4-fluorophenyl)-2-thienylmethyl]benzene form HxA seed crystals (for example prepared according to Example 1) and 2500 mL water and the obtained hazy suspension was cooled to 3° C. A different reactor was charged with 25.39 g crude 1-(β-D-glucopyranosyl)-4-methyl-3-[5-(4-fluorophenyl)-2-thienylmethyl]benzene (prepared in a similar manner as disclosed in Example 1 of WO 2005/012326 A1) and 75 mL ethanol. The obtained solution was filtered and subsequently cooled to 3° C. Thereafter, the cold ethanol solution was added to the cold aqueous seed crystal suspension in about 10 min under thorough stirring, whereat the temperature of the obtained mixture did not exceed 5° C. until the addition was complete. After complete addition the temperature of the obtained mixture was increased to 40° C. in 2 h and the mixture was stirred at the same temperature for 19 h. Finally, the mixture was cooled to 25° C. in 2 h before the crystals were collected by filtration and dried at 40° C. under vacuum (20-25 mbar) for 60 h to obtain 23.31 g of form HxA.

Yield: 91% of theory; XRPD: form HxA

Example 7

Preparation of 1-(β-D-glucopyranosyl)-4-methyl-3-[5-(4-fluorophenyl)-2-thienylmethyl]benzene form HxA—variable ethanol concentrations A reactor was charged with about 0.02 g 1-(β-D-glucopyranosyl)-4-methyl-3-[5-(4-fluorophenyl)-2-thienylmethyl]benzene form HxA seed crystals (for example prepared according to Example 1) and an amount of water according to Table 2 below. The obtained suspension was cooled to 3° C. A different reactor was charged with about 2.00 g crude 1-(6-D-glucopyranosyl)-4-methyl-3-[5-(4-fluorophenyl)-2-thienylmethyl]benzene (prepared in a similar manner as disclosed in Example 1 of WO 2005/012326 A1) and 6 mL ethanol. The obtained solution was filtered and subsequently cooled to 0-2° C. Thereafter, the cold ethanol solution was added to the cold aqueous seed crystal suspension under thorough stirring, whereat the temperature of the obtained mixture did not exceed 6° C. until the addition was complete. After complete addition the temperature of the mixture was increased to 40° C. in 2 h and the mixture was stirred at the same temperature for 16-20 h. Finally, the mixture was cooled to 25° C. in 1 h before the crystals were collected by filtration and dried at 40° C. under vacuum (20-25 mbar) overnight. The solid states of the obtained crystals were investigated by means of XRPD and the results are displayed in Table 2 below.

TABLE 2

Form HxA preparation using variable ethanol concentrations

| Example | Water [mL] | Ethanol [volume %] | Yield [% of theory] | XRPD |
|---|---|---|---|---|
| 7a | 200 | 2.9 | 87 | HxA |
| 7b | 100 | 5.7 | 91 | HxA |
| 7c | 50 | 10.7 | 94 | HxA |
| 7d | 40 | 13.0 | 93 | HxA |
| 7e | 35 | 14.6 | 92 | Hy0.5 |
| 7f | 24 | 20.0 | 89 | Hy0.5 |

As can be seen from Table 2 crystallizations from aqueous ethanol having an ethanol concentration of about 2.9 to 13.0 volume % resulted in form HxA, whereas ethanol concentrations of about ≥14.6 volume % lead to the building of form Hy0.5.

Example 8

Preparation of 1-(β-D-glucopyranosyl)-4-methyl-3-[5-(4-fluorophenyl)-2-thienylmethyl]benzene form HxA—diluted ethanol solution A reactor was charged with 0.02 g 1-(β-D-glucopyranosyl)-4-methyl-3-[5-(4-fluorophenyl)-2-thienylmethyl]benzene form HxA seed crystals (for example prepared according to Example 1) and 200 mL water and the obtained hazy suspension was cooled to 3° C. A different reactor was charged with 2.00 g crude 1-(β-D-glucopyranosyl)-4-methyl-3-[5-(4-fluorophenyl)-2-thienylmethyl]benzene (prepared in a similar manner as disclosed in Example 1 of WO 2005/012326 A1) and 24 mL ethanol. The obtained solution was filtered and subsequently cooled to 2° C. Thereafter, the cold ethanol solution was added to the cold aqueous seed crystal suspension in about 10 min under thorough stirring, whereat the temperature of the obtained mixture did not exceed 5° C. until the addition was complete. After complete addition the temperature of the mixture was increased to 40° C. in 2 h and the mixture was stirred at the same temperature for 19 h. Finally, the mixture was cooled to 25° C. in 1 h before the crystals were collected by filtration and dried at 40° C. under vacuum (20-25 mbar) overnight to obtain 1.78 g of form HxA.

Yield: 88% of theory; XRPD: Form HxA

Example 9

Preparation of 1-(β-D-glucopyranosyl)-4-methyl-3-[5-(4-fluorophenyl)-2-thienylmethyl]benzene form HxA—use of different water-miscible organic solvents A reactor was charged with about 0.02 g 1-(β-D-glucopyranosyl)-4-methyl-3-[5-(4-fluorophenyl)-2-thienylmethyl]benzene form HxA seed crystals (for example prepared according to Example 1) and 200 mL water and the obtained hazy suspension was cooled to 3° C. A different reactor was charged with about 2.00 g crude 1-(β-D-glucopyranosyl)-4-methyl-3-[5-(4-fluorophenyl)-2-thienylmethyl]benzene (prepared in a similar manner as disclosed in Example 1 of WO 2005/012326 A1) and 6 mL of a water-miscible organic solvent according to Table 3 below. The obtained solution was filtered and subsequently cooled to 0-2° C. Thereafter, the cold solution was added to the cold aqueous seed crystal suspension under thorough stirring, whereat the temperature of the obtained mixture did not exceed 5° C. until the addition was complete. After complete addition the temperature of the mixture was increased to 40° C. in 2 h and the mixture was stirred at the same temperature for 15-16 h. Finally, the mixture was cooled to 25° C. in 1 h before the crystals were collected by filtration and dried at 40° C. under vacuum (20-25 mbar) overnight. The solid states of the obtained crystals were investigated by means of XRPD and the results are displayed in Table 3 below.

TABLE 3

Form HxA preparation using different water-miscible organic solvents

| Example | Water-miscible organic solvent used | Yield [% of theory] | XRPD |
|---|---|---|---|
| 9a | THF | 89 | HxA |
| 9b | acetone | 89 | HxA |

Example 10

Preparation of 1-(β-D-glucopyranosyl)-4-methyl-3-[5-(4-fluorophenyl)-2-thienylmethyl]benzene form HxA—controlled addition of the solution to the seed crystal suspension at 25° C.

A reactor was charged with 0.02 g 1-(β-D-glucopyranosyl)-4-methyl-3-[5-(4-fluorophenyl)-2-thienylmethyl]benzene form HxA seed crystals (for example prepared according to Example 1) and 200 mL water and the obtained hazy suspension was stirred at 25° C. A different reactor was charged with 2.01 g crude 1-(β-D-glucopyranosyl)-4-methyl-3-[5-(4-fluorophenyl)-2-thienylmethyl]benzene (prepared in a similar manner as disclosed in Example 1 of WO 2005/012326 A1) and 6 mL ethanol. The obtained ethanol solution was filtered and dropwise added to the aqueous seed crystals suspension under thorough stirring, whereat the temperature of the obtained mixture was kept at 25° C. until the addition was complete. After complete addition the temperature of the mixture was increased to 40° C. in 2 h and the suspension was stirred at the same temperature for 22 h. Finally, the mixture was cooled to 25° C. in 1 h before the crystals were collected by filtration and dried at 40° C. under vacuum (20-25 mbar) overnight to obtain 1.81 g of form HxA.

Yield: 89% of theory, XRPD: form HxA

The experiment shows that there is no absolute necessity to keep the temperature of the obtained mixture at 0-15° C. during the addition of the solution to the aqueous seed crystal suspension in order to obtain form HxA as long as the water-miscible organic solvent concentration in the mixing zone of the mixture does not exceed the critical value of about 13 volume %. This can for example be achieved by a slow addition rate and thorough stirring.

Example 11

Preparation of 1-(β-D-glucopyranosyl)-4-methyl-3-[5-(4-fluorophenyl)-2-thienylmethyl]benzene form HxA—speedy addition of the product solution to the seed crystal suspension at 25° C.

A reactor was charged with 0.06 g 1-(β-D-glucopyranosyl)-4-methyl-3-[5-(4-fluorophenyl)-2-thienylmethyl]benzene form HxA seed crystals (for example prepared according to Example 1) and 600 mL water and the obtained hazy suspension was stirred at 25° C. A different reactor was charged with 6.02 g crude 1-(β-D-glucopyranosyl)-4-methyl-3-[5-(4-fluorophenyl)-2-thienylmethyl]benzene (prepared in a similar manner as disclosed in Example 1 of WO 2005/012326 A1) and 18 mL ethanol. The obtained solution was filtered and speedily added to the aqueous seed crystal suspension, whereat the temperature of the obtained mixture was kept at 25° C. until the addition was complete. After complete addition the obtained mixture was further stirred at 25° C. for 23 h. Finally, the crystals were collected by filtration and dried at 40° C. under vacuum (20-25 mbar) overnight to obtain 5.73 g of a mixture of form HxA and form Hy0.5.

Yield: 94% of theory, XRPD: form HxA+form Hy0.5

Without wishing to be bound by any theory the building of form Hy0.5 is most likely due to the fact that the water-miscible organic solvent concentration in the mixing zone of the mixture exceeded the critical value of about 13 volume % during the addition of the solution to the aqueous seed crystal suspension, which lead to the local crystallization of form Hy0.5 in this area. The risk for obtaining form Hy0.5 increases with increasing batch sizes and can be prevented either by a very slow and controlled addition rate (see e.g. Example 10 herein) or preferably by decreasing the temperature during the addition (see e.g. Examples 6 to 9 herein). Most preferably, both means are combined so that the ethanol solution is added in a controlled manner e.g. at a slow addition rate and under thorough stirring and the temperature of the mixture is kept at 0 to 15° C. (see for example Example 6 herein).

Example 12

Form HxA Preparation—Inverse Addition

A reactor was charged with 0.01 g 1-(β-D-glucopyranosyl)-4-methyl-3-[5-(4-fluorophenyl)-2-thienylmethyl]benzene form HxA seed crystals (for example prepared according to Example 1) and 100 mL water and the obtained hazy suspension was cooled to 3° C. A different reactor was charged with 1.02 g crude 1-(β-D-glucopyranosyl)-4-methyl-3-[5-(4-fluorophenyl)-2-thienylmethyl]benzene (prepared in a similar manner as disclosed in Example 1 of WO 2005/012326 A1) and 3 mL ethanol. The obtained solution was filtered and subsequently cooled to 3° C. Thereafter, the cold aqueous seed crystal suspension was added to the cold ethanol solution under thorough stirring, whereat the temperature of the obtained mixture did not exceed 5° C. until the addition was complete. After complete addition the temperature of the mixture was increased to 40° C. in 2 h and the mixture was stirred at the same temperature overnight. Finally, the mixture was cooled to 25° C. in 1 h before the crystals were collected by filtration and dried at 40° C. under vacuum (20-25 mbar) overnight to obtain 0.94 g form HxA.

Yield: 91% of theory; XRPD: form HxA

The experiment shows that the water-miscible organic solvent concentration of the obtained mixture is not critical with regards to the building of the wrong solid form as long as the temperature is kept at 0 to 15° C. until the addition of the aqueous seed crystal suspension to the solution is complete.

Example 13

Preparation of amorphous 1-(β-D-glucopyranosyl)-4-methyl-3-[5-(4-fluorophenyl)-2-thienylmethyl]benzene A solution of 12.99 g 1-(β-D-glucopyranosyl)-4-methyl-3-[5-(4-fluorophenyl)-2-thienylmethyl]benzene (prepared in a similar manner as disclosed in Example 1 of WO 2005/012326 A1) in 390 mL methylenechloride/acetone (2:1, volume:volume) was filtered and evaporated to dryness on a rotary evaporator at 40° C. under reduced pressure.

Figure 6:
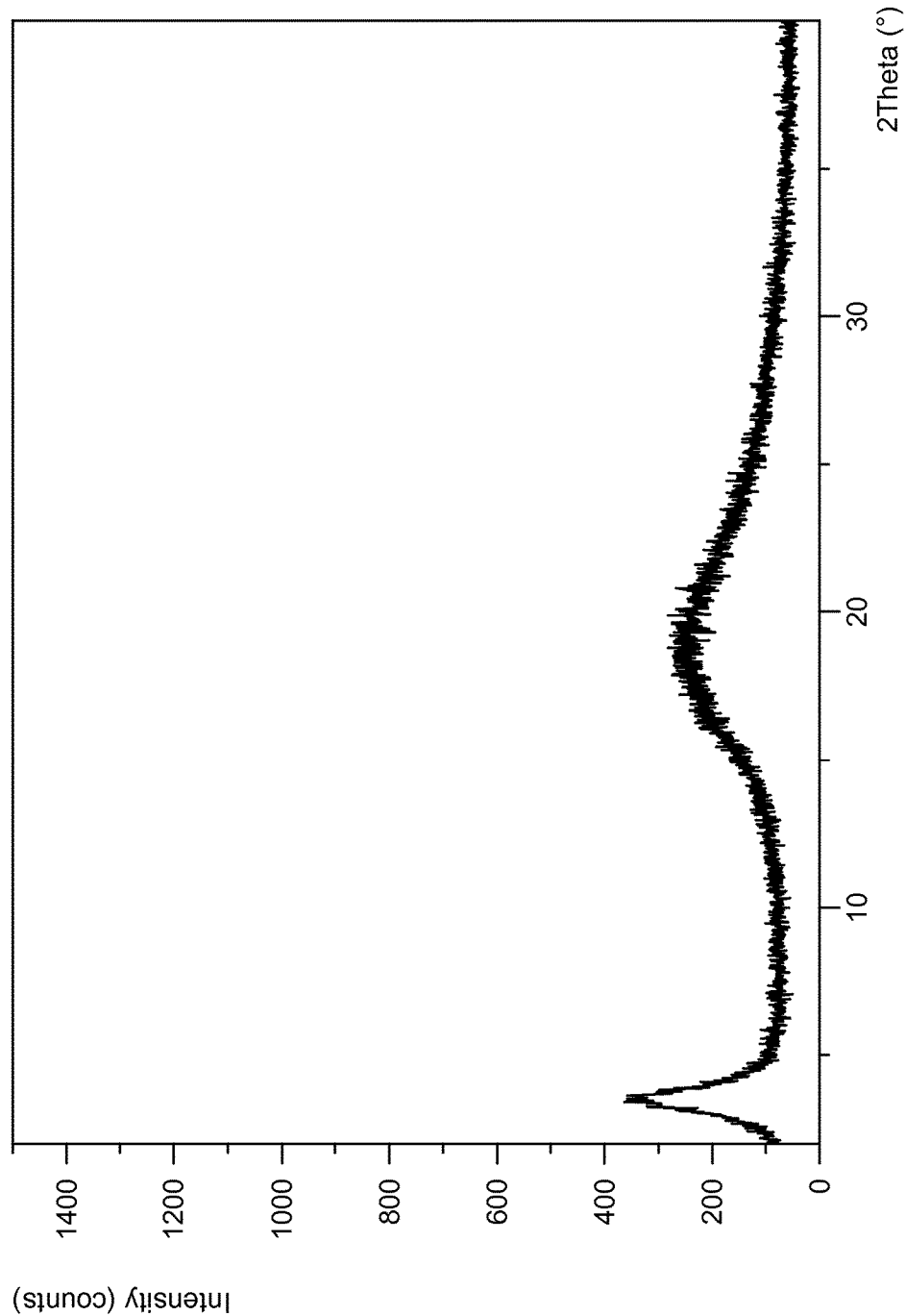
FIG. 6: XRPD of amorphous 1-(β-D-glucopyranosyl)-4-methyl-3-[5-(4-fluorophenyl)-2-thienylmethyl]benzene prepared according to Example 13

Yield: quantitative; XRPD: amorphous (the corresponding XRPD is displayed in FIG. 6 herein)

Example 14

Preparation of 1-(β-D-glucopyranosyl)-4-methyl-3-[5-(4-fluorophenyl)-2-thienylmethyl]benzene form HxB starting from form HxA 0.45 g of 1-(β-D-glucopyranosyl)-4-methyl-3-[5-(4-fluorophenyl)-2-thienylmethyl]benzene form HxA (for example prepared according to Example 6 herein) were stored at RT for 24 h in a desiccator over a saturated aqueous ammonium chloride solution providing an atmosphere having a RH of about 80% to obtain form HxB quantitatively.

Yield: quantitative; XRPD: form HxB

Reference Example 1

Repetition of Example 2 of WO 2008/069327 A1 Using Form HxA Seed Crystals 4.00 g amorphous 1-(β-D-glucopyranosyl)-4-methyl-3-[5-(4-fluorophenyl)-2-thienylmethyl]-benzene (prepared according to Example 13 herein) were dissolved in 40 mL acetone at 25° C. To the solution 80 mL water and 0.04 g form HxA seed crystals were added. The mixture was stirred for 19 h at 25° C., whereat an emulsion was obtained. The addition of further 0.16 g form HxA seed crystals lead to the precipitation of a solid material and the obtained suspension was further stirred for 6 h at 25° C. before the crystals were collected by filtration and dried at RT under vacuum (20-25 mbar) for 65.5 h to obtain 2.78 g form Hy0.5.

Yield: 66% of theory; XRPD: form Hy0.5

Reference Example 2

Repetition of Reference Example 1 at Decreased Temperature 4.01 g amorphous 1-(β-D-glucopyranosyl)-4-methyl-3-[5-(4-fluorophenyl)-2-thienylmethyl]-benzene (prepared according to Example 13 herein) were dissolved in 40 mL acetone and subsequently cooled to 3° C. To the solution 80 mL of precooled water and 0.04 g form HxA seed crystals were added, whereat the temperature did not exceed 7° C. during the addition. The obtained suspension was warmed to 25° C. and further stirred at the same temperature for 18.5 h. Finally, the obtained crystals were collected by filtration and dried at RT under vacuum (20-25 mbar) for 71 h to obtain 2.83 g of form Hy0.5.

Yield: 70% of theory; XRPD: form Hy0.5 (the corresponding XRPD is displayed in FIG. 5 herein)

In Reference Example 1 as well as in Reference Example 2 the water-miscible organic solvent concentration of the obtained solvent mixture was about 33 volume %, which caused the building of form Hy0.5 in both examples.

The invention claimed is:

1. A pharmaceutical composition comprising a pharmaceutically acceptable carrier and an effective amount of a crystalline form of a non-stoichiometric hydrate of the compound of formula (I)

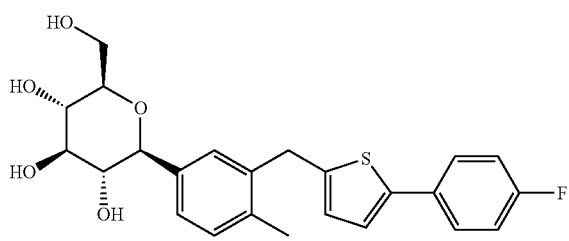

(I)

wherein the crystalline non-stoichiometric hydrate of the compound of formula (I) is characterized by an X-ray powder diffractogram comprising peaks at 2-Theta angles of 5.4±0.2°, 6.7±0.2°, 13.2±0.2°, 16.1±0.2°, 19.6±0.2° and 24.1±0.2° or 6.6±0.2°, 7.3±0.2°, 12.2±0.2°, 15.4±0.2°, 19.9±0.2° and 23.9±0.2°.

2. The pharmaceutical composition according to claim 1, wherein the crystalline form comprises a water content in the range of 0.1 to 8.0%.

3. The pharmaceutical composition according to claim 1, wherein the crystalline form has an X-ray powder diffraction pattern comprising peaks at 2-theta angles of 5.4±0.2°, 6.7±0.2°, 13.2±0.2°, 16.1±0.2°, 19.6 and 24.1±0.2°.

4. The pharmaceutical composition according to claim 1, wherein the crystalline form has an X-ray powder diffraction pattern comprising peaks at 2-theta angles of 6.6±0.2°, 7.3±0.2°, 12.2±0.2°, 15.4±0.2°, 19.9 and 23.9±0.2°.

5. The pharmaceutical composition according to claim 1, wherein the crystalline form has an X-ray powder diffraction pattern substantially the same as the X-ray powder diffraction pattern shown in FIG. 1 when measured using CuKα radiation.

6. The pharmaceutical composition according to claim 1, wherein the crystalline form has an X-ray powder diffraction pattern substantially the same as the X-ray powder diffraction pattern shown in FIG. 3 when measured using CuKα radiation.

7. A process for the preparation of the crystalline form according to claim 3 comprising the steps of:
   (d) forming a suspension of amorphous 1-(β-D-glucopyranosyl)-4-methyl-3-[5-(4-fluorophenyl)-2-thienylmethyl]benzene in water;
   (e) subjecting the suspension to a mechanical particle size reduction process;
   (f) isolating the obtained crystals; and
   (g) subjecting the crystals to an atmosphere having a relative humidity of ≤30% at 20±5° C.

8. A process for the preparation of the crystalline form according to claim 4 comprising the steps of:
   (a) forming a suspension of amorphous 1-(β-D-glucopyranosyl)-4-methyl-3-[5-(4-fluorophenyl)-2-thienylmethyl]benzene in water;
   (b) subjecting the suspension to a mechanical particle size reduction process;
   (c) isolating the obtained crystals; and
   (d) subjecting the crystals to an atmosphere having a relative humidity of ≥45% at 20±5° C.

9. A process for the preparation of a crystalline form-of a non-stoichiometric hydrate of the compound of formula (I)

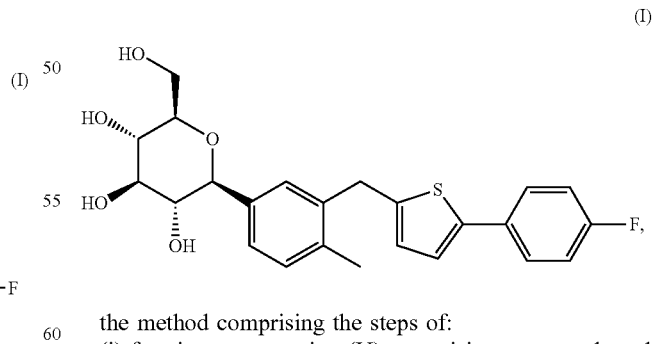

(I)

the method comprising the steps of:
   (i) forming a suspension (U) comprising water and seed crystals of the compound of formula (I),
   (ii) forming a solution (O) comprising a water-miscible organic solvent and the compound of formula (I),
   (iii) forming a mixture (M) comprising not more than 13 volume % of a water miscible-organic solvent by combining solution (O) and suspension (U) and (iv) crystallizing the compound of formula (I),
wherein the seed crystals are characterized by a X-ray powder diffractogram comprising characteristic peaks at 2-Theta angles of 5.4±0.2°, 6.7±0.2°, 13.2±0.2°, 16.1±0.2°, 19.6±0.2° and 24.1±0.2° and/or 6.6±0.2°, 7.3±0.2°, 12.2±0.2°, 15.4±0.2°, 19.9±0.2° and 23.9±0.2° when measured at a temperature between 15 and 25° C. using Cu-Kα radiation having a wavelength of 0.15419 nm.

10. The process according to claim 9, wherein the crystals of the compound of formula (I) obtained in step (iv) are isolated and subjected to an atmosphere having a relative humidity of ≤30% at 20±5° C.

11. The process according to claim 9, wherein the crystals of the compound of formula (I) obtained in step (iv) are isolated and subjected to an atmosphere having a relative humidity of ≥45% at 20±5° C.

12. A pharmaceutical composition according to claim 1 for use as a medicament.

13. A pharmaceutical composition according to claim 1 for use in the treatment of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis and/or hypertension.

14. A pharmaceutical composition comprising an effective amount of a crystalline form according to claim 1 and metformin.

15. A pharmaceutical composition comprising a pharmaceutically acceptable carrier and an effective amount of a crystalline non-stoichiometric hydrate of the compound of formula (I)

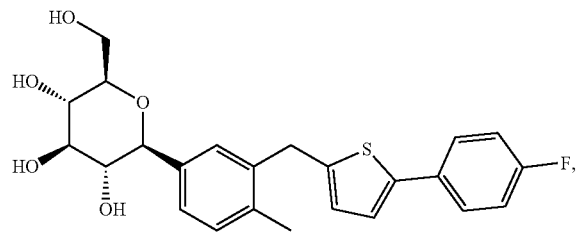

wherein the crystalline non-stoichiometric hydrate is prepared by:
(a) forming a suspension of amorphous 1-(β-D-glucopyranosyl)-4-methyl-3-[5-(4-fluorophenyl)-2-thienylmethyl]benzene in water;
(b) subjecting the suspension to a mechanical particle size reduction process; and
(c) isolating the obtained crystals,
wherein the crystals are lath-shaped, and
wherein the crystalline non-stoichiometric hydrate of the compound of formula (I) is characterized by an X-ray powder diffractogram comprising characteristic peaks at 2-Theta angles of 5.4±0.2°, 6.7±0.2°, 13.2±0.2°, 16.1±0.2°, 19.6±0.2° and 24.1±0.2° or 6.6±0.2°, 7.3±0.2°, 12.2±0.2°, 15.4±0.2°, 19.9±0.2° and 23.9±0.2° when measured at a temperature between 15 and 25° C. using Cu-Kα radiation having a wavelength of 0.15419 nm.

* * * * *